(12) United States Patent
Johnson et al.

(10) Patent No.: US 8,978,452 B2
(45) Date of Patent: Mar. 17, 2015

(54) WETNESS SENSOR USING RF CIRCUIT WITH FRANGIBLE LINK

(75) Inventors: Justin M. Johnson, Oakdale, MN (US); Lori-Ann S. Prioleau, St. Paul, MN (US); Brinda B. Badri, Woodbury, MN (US); James C. Vanous, Roseville, MN (US); Robert D. Lorentz, North Oaks, MN (US); Jacob D. Chatterton, St. Paul, MN (US); Steven J. Perron, St. Paul, MN (US); Donald R. Battles, Arden Hills, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 456 days.

(21) Appl. No.: 13/207,505

(22) Filed: Aug. 11, 2011

(65) Prior Publication Data

US 2013/0036802 A1 Feb. 14, 2013

(51) Int. Cl.
*G01N 25/26* (2006.01)
*G01N 27/22* (2006.01)
*A61F 13/42* (2006.01)

(52) U.S. Cl.
CPC .............. *G01N 27/223* (2013.01); *A61F 13/42* (2013.01)
USPC ................................ 73/74; 340/604; 604/361

(58) Field of Classification Search
CPC ........................................................ G01N 25/56
USPC .................... 73/74; 340/604; 604/358, 361
See application file for complete search history.

(56) References Cited

U.S. PATENT DOCUMENTS

| | | |
|---|---|---|
| 5,004,700 A | 4/1991 | Webb et al. |
| 5,348,761 A | 9/1994 | Mitter et al. |
| 6,091,607 A | 7/2000 | McKeown et al. |
| 6,373,395 B1 * | 4/2002 | Kimsey ...................... 340/602 |
| 6,583,722 B2 | 6/2003 | Jeutter et al. |
| 6,603,403 B2 * | 8/2003 | Jeutter et al. ................. 340/604 |

(Continued)

FOREIGN PATENT DOCUMENTS

| | | |
|---|---|---|
| JP | 2007-240470 | 9/2007 |
| WO | WO 96/14813 | 5/1996 |

(Continued)

OTHER PUBLICATIONS

U.S. Appl. No. 13/207,522, "Wetness Sensors", filed on even date herewith.

(Continued)

*Primary Examiner* — Hezron E Williams
*Assistant Examiner* — Hoang Nguyen
(74) *Attorney, Agent, or Firm* — X. Christina Huang

(57) ABSTRACT

A wetness sensor includes a substrate that carries a tuned RF circuit. The circuit includes a conductive pattern applied to the substrate, a capacitor, and a jumper all disposed on a same side of the substrate. The conductive pattern includes an inductive coil, and an inner and outer terminus. The jumper electrically couples the inner terminus to the outer terminus. The jumper also includes a frangible link which, when contacted by a target fluid, produces a drastic change in the operation of the RF circuit. The drastic change can be interpreted by a remote reader as a "wet" condition. Contact of the frangible link by the target fluid may change the impedance or resistance of the RF circuit by at least a factor of 5, 10, 100, or more, and/or may cause the frangible link to disintegrate to produce an open circuit, and/or may substantially render the RF circuit inoperative.

27 Claims, 11 Drawing Sheets

(56) References Cited

U.S. PATENT DOCUMENTS

| | | | |
|---|---|---|---|
| 6,677,859 B1* | 1/2004 | Bensen | 340/604 |
| 6,774,800 B2* | 8/2004 | Friedman et al. | 340/573.5 |
| 6,832,507 B1* | 12/2004 | van de Berg et al. | 73/73 |
| 7,141,715 B2 | 11/2006 | Shapira | |
| 7,250,547 B1* | 7/2007 | Hofmeister et al. | 604/361 |
| 7,456,744 B2* | 11/2008 | Kuhns et al. | 340/572.1 |
| 7,460,015 B2 | 12/2008 | Forster et al. | |
| 7,477,151 B2* | 1/2009 | Forster et al. | 340/572.3 |
| 7,629,888 B2 | 12/2009 | Forster et al. | |
| 7,812,731 B2 | 10/2010 | Bunza et al. | |
| 7,839,352 B2 | 11/2010 | Strauser et al. | |
| 7,843,317 B2 | 11/2010 | Angell et al. | |
| 7,977,529 B2 | 7/2011 | Bergman et al. | |
| 8,199,016 B2 | 6/2012 | Forster et al. | |
| 2002/0187181 A1 | 12/2002 | Godbey et al. | |
| 2004/0064114 A1 | 4/2004 | David et al. | |
| 2004/0070510 A1* | 4/2004 | Zhang et al. | 340/618 |
| 2006/0058745 A1 | 3/2006 | Pires | |
| 2007/0083174 A1 | 4/2007 | Ales, III et al. | |
| 2007/0252710 A1 | 11/2007 | Long et al. | |
| 2008/0132859 A1 | 6/2008 | Pires | |
| 2008/0150732 A1 | 6/2008 | Bunza et al. | |
| 2008/0266123 A1* | 10/2008 | Ales et al. | 340/604 |
| 2008/0269702 A1 | 10/2008 | Ales et al. | |
| 2008/0300559 A1* | 12/2008 | Gustafson et al. | 604/361 |
| 2009/0326491 A1* | 12/2009 | Long et al. | 604/361 |
| 2010/0079287 A1 | 4/2010 | Forster et al. | |
| 2010/0100026 A1* | 4/2010 | Morris | 604/5.04 |
| 2011/0263952 A1 | 10/2011 | Bergman et al. | |
| 2011/0309937 A1 | 12/2011 | Bunza et al. | |

FOREIGN PATENT DOCUMENTS

| | | |
|---|---|---|
| WO | WO 00/79497 A1 | 12/2000 |
| WO | WO 02/032049 | 11/2002 |
| WO | WO 2004/021944 | 3/2004 |
| WO | WO 2008/052811 | 5/2008 |
| WO | WO 2008/069753 | 6/2008 |
| WO | WO 2008/075227 | 6/2008 |

OTHER PUBLICATIONS

Mohan et al., "Simple Accurate Expressions for Planer Spiral Inductances," IEEE Journal of Solid-State Circuits, 36, 1419-1424, Oct. 1999.

* cited by examiner

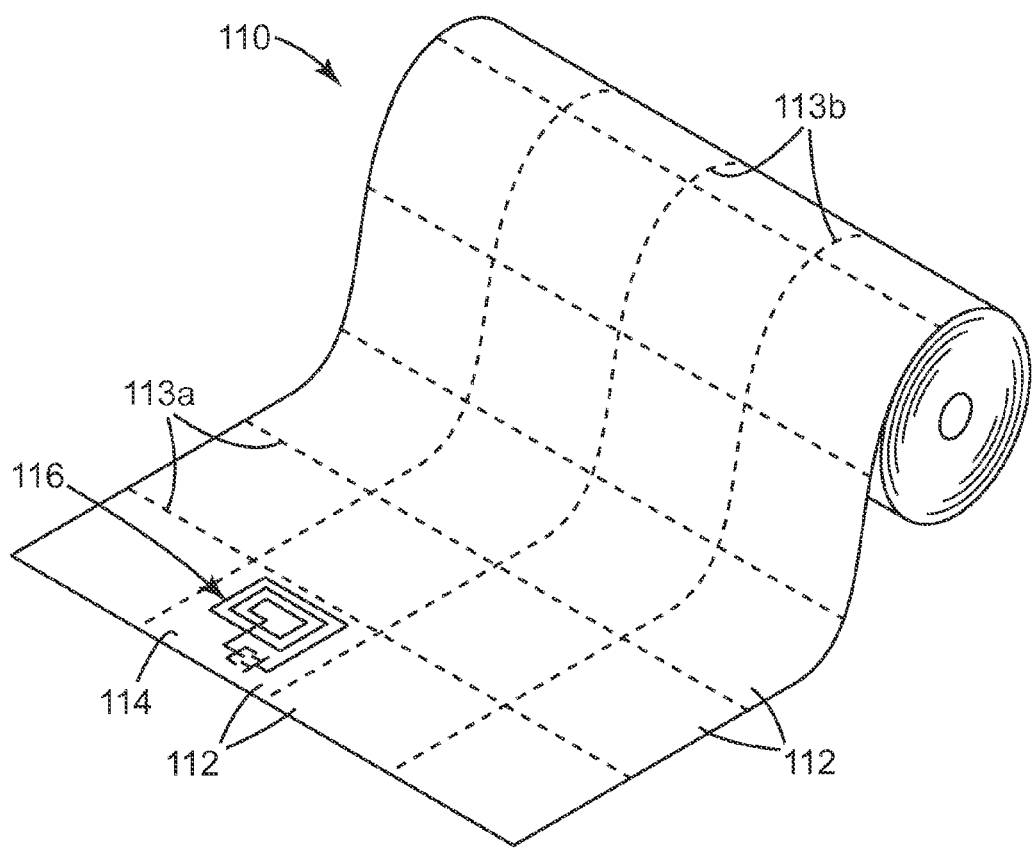
*Fig. 1*
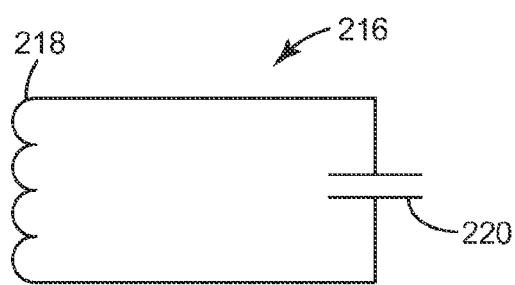 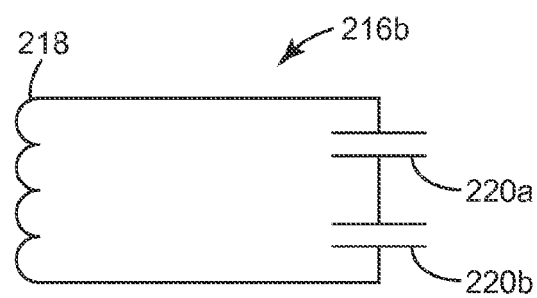
*Fig. 2a*  *Fig. 2b*

WETNESS SENSOR USING RF CIRCUIT WITH FRANGIBLE LINK

FIELD OF THE INVENTION

This invention relates generally to wetness sensors, as well as articles and systems that incorporate such sensors, and methods pertaining to such sensors.

BACKGROUND

Millions of young and old wear diapers every day. For both of these groups, checking for wetness may require relying on others. In the case of adult patients who are wearing a diaper due to a medical condition or life situation, an unnoticed wet diaper can become a health risk to the occupant in some circumstances. Diaper rash and skin ulcers are just two possible medical conditions that may result from prolonged exposure to wetness. For both the health risk to the patient and the possible monetary liability for the health care provider, processes and procedures for enhanced diaper monitoring are desirable.

In some places, standard monitoring procedures for adult patients requiring the use of a diaper is to monitor the patient for incontinence at least once every four hours. If the patient is unable to communicate the state of the diaper on their own, a physical check of the diaper is required by the caregiver. Physically turning the patient is commonly required in order to make a satisfactory physical check. This can pose a health risk to the nurse or work staff, and, for heavier patients, additional personnel or even a mechanical lifting device may be required. Eliminating this time consuming and undignified procedure, by interrogating the state of the diaper without performing a physical check, would be highly desirable.

Others have proposed wetness sensors for use in diapers. See, for example, U.S. Patent Application Publication US 2008/0300559 (Gustafson et al.). See also U.S. Patent Application Publications US 2004/0064114 (David et al.), US 2004/0070510 (Zhang et al.), US 2005/0156744 (Pires), US 2006/0058745 (Pires), US 2007/0083174 (Ales, III et al.), US 2008/0132859 (Pires), and US 2008/0266123 (Ales et al.), and U.S. Pat. No. 6,373,395 (Kimsey), U.S. Pat. No. 6,583,722 (Jeutter et al.), U.S. Pat. No. 6,603,403 (Jeutter et al.), and U.S. Pat. No. 6,774,800 (Friedman et al.). Nevertheless, the widespread use of wetness sensors in diapers—and other applications—has yet to be realized.

BRIEF SUMMARY

We have developed a family of sensors that can detect wetness and that can be remotely interrogated. These sensors are also compatible with low cost manufacturing techniques. We have found that the sensors can be adapted not only for use in diapers or other absorbent garments, but also in other end use applications in which it is desirable to detect wetness but difficult to visually or otherwise directly observe the wetness. Such other applications may involve incorporating the wetness sensors in construction-related articles such as wall board, insulation, flooring, roofing, and fittings and support structures to detect leakage from pipes underground, beneath floors, behind walls, or above ceilings, for example. Other applications may involve incorporating the wetness sensors in packages or boxes to detect leakage or thawing, e.g. for medical or automotive applications, for example.

We describe herein, among other things, sensors that include a first substrate that carries a tuned RF circuit. The circuit includes a conductive pattern applied to the first substrate, a capacitor, and a jumper all disposed on a same side of the first substrate. The conductive pattern includes an inductive coil, and an inner and outer terminus. The jumper electrically couples the inner terminus to the outer terminus. The jumper also includes a frangible link which, when contacted by a target fluid, produces a drastic change in the operation of the RF circuit. The drastic change can be interpreted by a remote reader as a "wet" condition. Contact of the frangible link by the target fluid may change the impedance or resistance of the RF circuit by at least a factor of 5, 10, 100, or 1000, and/or may cause the frangible link to disintegrate to produce an open circuit, and/or may substantially render the RF circuit inoperative.

The capacitor may comprise first and second capacitor plates, the first capacitor plate selected from one of the inner and outer terminuses of the conductive pattern, and the second capacitor plate selected from a first or second terminus of the jumper. The capacitor may also include a first dielectric material disposed between the first and second capacitor plates, the first dielectric material being soluble in the target fluid to provide the frangible link.

The tuned RF circuit may also include a second capacitor disposed at an opposite terminus of the jumper relative to the first-mentioned capacitor, the second capacitor having a second dielectric material disposed between third and fourth capacitor plates, the second material also being soluble in the target fluid and also being part of the frangible link.

The frangible link may alternatively or in addition include an adhesive that connects the jumper to the substrate, and that is soluble in the target fluid. Alternatively or in addition, the jumper may include a conductive member disposed on a second substrate, and the second substrate may be adapted to dissolve, swell, or otherwise degrade in the target fluid to provide the frangible link.

In some cases, the first dielectric material, the second dielectric material, and/or the second substrate may be or include polyvinyl alcohol (PVA). In some cases, the target fluid comprises a polar liquid, such as water, or one or more aqueous human body fluids.

In some cases, the second substrate is a self-supporting film, and the conductive member of the jumper is not self-supporting. In some cases, the conductive member of the jumper has a thickness of less than 1 micron, or less than 100 nanometers. In some cases, the conductive member has a variable thickness and/or variable width. In some cases, the electrically conductive trace has a variable thickness, the thickness variation being associated with a structured interface between the conductive member and the second substrate.

The sensor may include a skin-compatible adhesive disposed on an outer surface of the sensor. Such an adhesive may comprise silicone.

Absorbent garments such as diapers, as well as other articles, that incorporate the disclosed wetness sensors are also disclosed. In the case of an absorbent garment, the garment may include a liquid-permeable sheet, a liquid-impermeable sheet, and an absorbent material trapped between the liquid-permeable sheet and the liquid-impermeable sheet. The wetness sensor may be disposed between the liquid-permeable sheet and the liquid-impermeable sheet, or between the liquid-permeable sheet and a user's body. Preferably, the wetness sensor is disposed between the liquid-impermeable sheet and the absorbent core so that it will degrade when the core is saturated and will not be triggered by the release of only a small amount of target fluid.

Articles used in building construction that incorporate the disclosed wetness sensors are also disclosed. Such construction articles may be or include wall board, insulation, flooring (including without limitation carpeting), roofing, and/or fitting(s) or support structure(s) for pipe(s).

We describe systems in which at least one of the disclosed wetness sensors is combined with a reader configured to remotely assess a condition of the tuned RF circuit so as to assess the condition of the sensor. The reader may be configured for mounting in or on a mobile or stationary support for a person, e.g., a bed, chair (including e.g. a wheel-chair or rocking chair), cart, or other mobile or stationary support.

Related methods, systems, and articles are also discussed.

These and other aspects of the present application will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

FIG. 1 is a schematic perspective view of a rolled-up sheet or web containing a large number of wetness sensors before slitting or otherwise converting the sheet into individual sensor tags;

FIGS. 2a and 2b are schematic circuit diagrams of exemplary wetness sensors;

FIG. 11b is a graph of modeled data for an embodiment of the circuit of FIG. 11a;

FIG. 14b is a schematic cross-sectional view taken along lines 14b-14b in FIG. 14a.

In the figures, like reference numerals designate like elements.

DETAILED DESCRIPTION OF ILLUSTRATIVE EMBODIMENTS

Figure 2C:
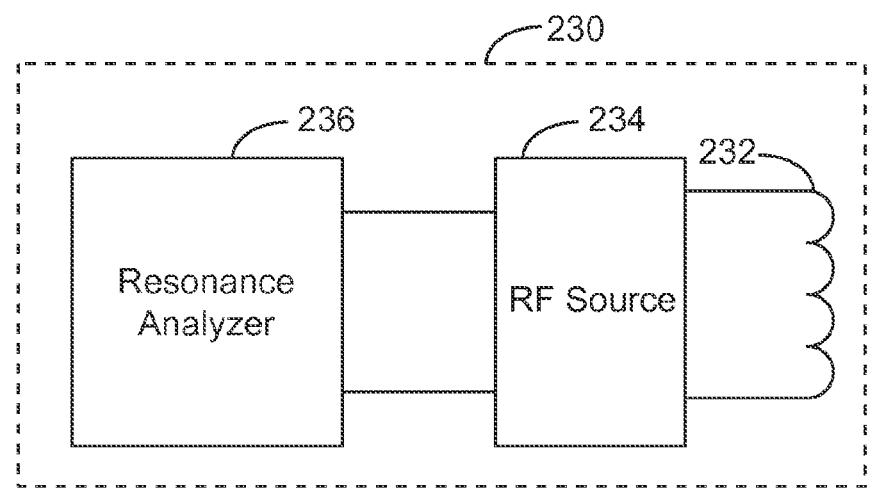
FIG. 2c is a schematic block diagram of an exemplary remote interrogation device or reader.

In FIG. 1, we see a rolled-up sheet or web 110 which may be fabricated using high volume film handling equipment. The web 110 includes a flexible substrate 114 to which an electrically conductive pattern or trace has been applied, the pattern forming at least a portion of a tuned RF circuit 116. The trace typically forms at least an inductive coil, but it may also include other distinct circuit elements and connection features, as exemplified more fully below. The conductive pattern, as well as the remainder of the RF circuit, is thus carried by the substrate 114.

Although only one circuit 116 is shown in the figure, the reader will understand that substantially the same or similar tuned RF circuits are preferably provided in an array on the web, one such circuit being disposed in each region labeled 112, and all such circuits preferably being disposed on the same side of the web 110. The reference number 112 may thus refer to individual sensors in the form of tags or labels that may be obtained by converting web 110 by slitting or cutting operations along lines 113a, 113b, for example.

The tuned RF circuit 116 also includes one or more discrete circuit elements in addition to the electrically conductive pattern. For example, the circuit 116 includes at least a separate jumper (an electrically conductive linking member) and an optional discrete capacitor, as discussed further below, that are carried by the substrate 114 and connected to the conductive pattern so as to complete the RF circuit 116 and provide the desired functionality. In some cases, the conductive pattern may itself include one or more capacitors, in addition to an inductive coil. If desired, any discrete circuit elements that form part of the RF circuit 116 may be attached to the substrate 114, or to a portion of the RF circuit 116, after slitting or cutting the web into individual sensor tags 112, rather than before such slitting or cutting. Alternatively, one or more discrete circuit elements may be attached to the substrate 114, or to a portion of the RF circuit 116, while the web 110 is still intact, before subdividing the web into the individual tags. The conductive pattern and other component(s) of the RF circuit 116 are preferably carried by the substrate and disposed on only one side of the substrate 114. Such an arrangement is advantageous from a manufacturing standpoint so that only one-sided film processing can be employed.

The substrate 114 is not only flexible, but is also preferably self-supporting. In this regard, a substrate is said to be self-supporting if it has a mechanical integrity sufficient to permit handling of the substrate without undue breakage, tears, or other damage that would make it unsuitable for its intended application.

Significantly, the circuit 116 includes a frangible link that is associated with a jumper component of the circuit. The frangible link may comprise a conductive or non-conductive adhesive that connects the jumper or a portion thereof to the sensor substrate, the adhesive being adapted to dissolve when contacted by water or another target fluid. The frangible link may alternatively or in addition comprise a second substrate that forms part of the jumper, the second substrate being adapted to dissolve, swell, or otherwise degrade when contacted by the target fluid. The second substrate may be self-supporting, and a conductive member disposed on the second substrate, and forming part of the jumper, is preferably not self-supporting. With these design features, exposure of the sensor tag to the target fluid can produce a drastic change in the physical structure of the RF circuit, and a corresponding drastic change in the operation of the RF circuit, the latter of which can be interpreted by a remote reader or interrogation device as a "wet" condition. For example, when the frangible link is contacted by the target fluid, the conductive member of the jumper, or a portion thereof, may simply collapse, crumble, or fall apart.

The drastic change in operation of the RF circuit may be manifested by a change in resistance or impedance of the circuit by at least a factor of 5, 10, 100, or 1000, for example. In this regard, a "change in resistance or impedance" refers to a change in the magnitude of the resistance or impedance. Impedance extends the concept of direct current (DC) resistance to alternating current (AC) circuits, describing not only the relative amplitudes of the voltage and current, but also the relative phases. Impedance describes a measure of opposition to alternating current and is described by a complex number. The real part of impedance describes the resistance (amplitude ratio of voltage and current), and the imaginary part describes the phase differences. Phase differences only occur when the circuit has a capacitive or inductive component, and typically a plus sign is used to indicate the inductance of the imaginary part and a negative sign is used to indicate the capacitance of the imaginary part. An impedance analyzer works by measuring the ratio of voltage to current through the electronic circuit.

Alternately or in addition, the drastic change in operation of the RF circuit may be manifested by a change in resonant frequency, Q-factor, bandwidth, amplitude, and/or other resonant characteristic. Alternatively or in addition, the drastic change in operation may be manifested by a substantial disintegration or break-up of the jumper or a portion thereof so as to provide the RF circuit with an open circuit. Alternatively or in addition, the drastic change in operation may be manifested by the RF circuit being rendered substantially inoperative.

Exemplary tuned RF circuits suitable for use in the disclosed wetness sensors are shown schematically in FIGS. 2a and 2b. In FIG. 2a, a simple RF circuit 216 comprises an inductor 218 and a capacitor 220 connected as shown. The inductance L and capacitance C of these components combine to provide the LC circuit 216, the circuit having a resonant frequency f (expressed in units of cycles per second, or Hertz) given by:

$$f = \frac{1}{2\pi\sqrt{LC}}.$$

The values of L and C are preferably selected so that the resonant frequency is tuned to a desired portion of the radio frequency (RF) electromagnetic spectrum, e.g., a desired portion of the spectrum from 30 kHz to 300 GHz. In preferred embodiments the resonant frequency may be in a desired portion of the narrower range from 1 to 100 MHz, or more specifically at a target frequency of 13.56 MHz, for example. In any case, the tuned RF frequency of the sensor circuit is preferably selected to be compatible with (e.g. to substantially match, overlap with, or fall within) a frequency range of a remote reader or interrogation device, the reader and the RF circuit of the sensor thus operating as a wetness detection system. The inductor 218 acts as an antenna to receive RF electromagnetic energy from the reader if the energy is close to the resonant frequency of the circuit, and the inductor 218 then re-emits at least some of the absorbed energy at or near the circuit's resonant frequency.

The RF circuit 216b of FIG. 2b is similar to circuit 216, except that the single capacitor 220 has been replaced with two separate capacitors 220a, 220b connected in series. In alternative embodiments, more than two separate capacitors may be used, and they all may be connected in series or they may be connected in other ways. Furthermore, although only one inductor coil is preferred in the disclosed RF circuits, embodiments having more than one inductor are also contemplated. In some embodiments, the various elements of the RF circuit are connected to each other in such a way as to provide an RF circuit whose response can be approximated by the simple LC resonant circuit of FIG. 2a. For example, the individual capacitors 220a, 220b of FIG. 2b can be mathematically represented by a single capacitor 220 having an appropriate capacitance C. The values of the various circuit elements making up the RF circuit (e.g. the inductance of inductor 218, and the capacitances of capacitors 220a, 220b) are again selected to provide a resonant frequency tuned to a desired portion of the RF spectrum, as discussed above. Virtually all real circuits contain some amount of resistance. In some embodiments of the disclosed wetness sensors, the RF circuit may have a resistance that is negligible, while in other cases the RF circuit may have a non-negligible resistance. In the latter cases, the RF circuit may include one or more individual resistors, e.g., to form an RLC resonant circuit.

In some cases, additional circuitry (not shown) may be included in the tuned RF circuit for emitting an identification code via the antenna. Such additional circuitry can be the same as or similar to circuitry used in known radio frequency identification (RFID) devices. Devices that are capable of transmitting a code to the reader are typically referred to as RFID devices. Devices not capable of transmitting an identification code are sometimes referred to as electronic article surveillance (EAS) devices. EAS devices absorb and disrupt an electromagnetic field, such as an RF field, emitted by a reader. The disruption of the field may be detected by the reader and interpreted to indicate the presence of an EAS device. The tuned RF circuits used in the disclosed wetness sensors are preferably of the generally simpler EAS design, although other designs are contemplated, including but not limited to the more complex RFID design. Preferred tuned RF circuits are passive in nature, i.e., they do not incorporate a battery or other on-board source of power, but instead derive power from coupling to the electromagnetic field emitted by the reader antenna. In some cases, however, depending on the end-use application of the wetness sensor, the tuned RF circuit may be active in nature, i.e., it may include a battery or other power source. In any case, the tuned RF circuit is typically characterized by a resonant frequency and a circuit impedance.

FIG. 2c is a schematic block diagram of an exemplary remote interrogation device or reader 230. The reader 230 includes an inductor 232, an RF source 234, and a resonance analyzer 236. Energy is stored in the fields surrounding the inductor 232, which serves as an antenna. This stored energy may be coupled to the tuned RF circuit of a wetness sensor if the wetness sensor is in the vicinity of the reader 230. The resonance analyzer 236 may be configured to detect changes in the amount of energy coupled from the antenna of the reader 230 to the tuned RF circuit, such coupling occurring if the resonant frequency of the tuned RF circuit is sufficiently near the resonant frequency of the reader circuit. Perturbations in the interrogator signal that are attributable to changes in the energy coupled by the tuned RF circuit can be considered to constitute a sensing signal or sensing circuit signal.

Figure 3A:
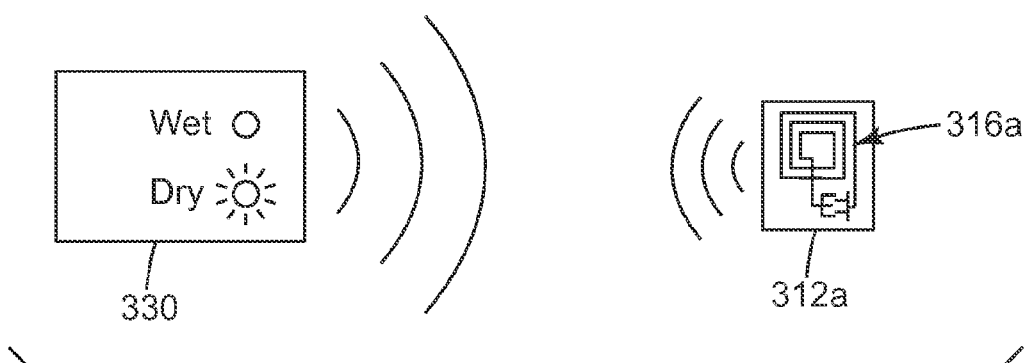
FIG. 3a is a schematic diagram of a detection system including a wetness sensor and a reader, where the wetness sensor is in a "dry" state.
Figure 3B:
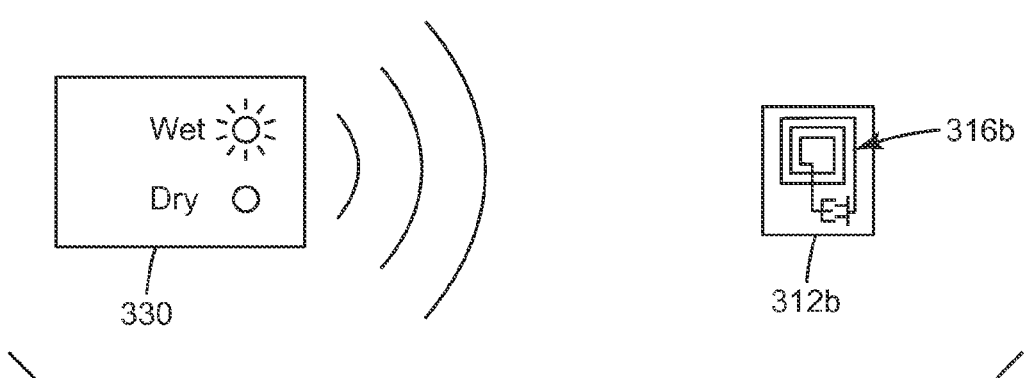
FIG. 3b is a schematic diagram similar to that of FIG. 3a, but where the wetness sensor is in a "wet" state.

FIGS. 3a and 3b are schematic diagrams of a detection system including a wetness sensor and a reader 330. In FIG.

3a, the wetness sensor 312a is in a "dry" state, and in FIG. 3b the wetness sensor has been contacted by water or another target fluid to produce the wetness sensor 312b in a "wet" state.

In FIG. 3a, the reader 330 broadcasts an RF signal, at least a portion of which has a suitable frequency component that can be absorbed by the tuned RF circuit 316a of the sensor 312a. The circuit 316a includes a frangible link that is intact. The sensor 312a converts some of the absorbed energy to a (weaker) sensing signal, which is broadcast by the circuit 316a and sensed by the reader 330. The reader 330 interprets the sensing signal from the circuit 316a as a "dry" condition, and an indicator light or other suitable status output may be provided by the reader 330.

In FIG. 3b, the reader 330 again broadcasts the same RF signal. The sensor 312b is in the vicinity of the reader just as sensor 312a was, but exposure of the sensor to the target fluid has caused the frangible link to wholly or partially fail, e.g., by causing a jumper substrate to partially or completely dissolve, or to swell or otherwise degrade. A tuned RF circuit 316b is shown in the figure, but the circuit may be wholly or partially inoperative as a result of the complete or partial failure of the frangible link. Alternatively, the circuit may remain operative, but it may have very different characteristics from those of circuit 316a, e.g., very different impedance, very different resonant frequency, Q-factor, bandwidth, amplitude, and/or other resonant characteristic. Consequently, the sensor 312b may provide no sensing signal, or it may provide a sensing signal that is drastically different from the sensing signal provided by the sensor 312a before contact with the target fluid. The reader 330 interprets the absence of a sensing signal, or the drastically different sensing signal, as a "wet" condition. A "wet" indicator light or other suitable status output may then be provided by the reader 330.

Figure 4:
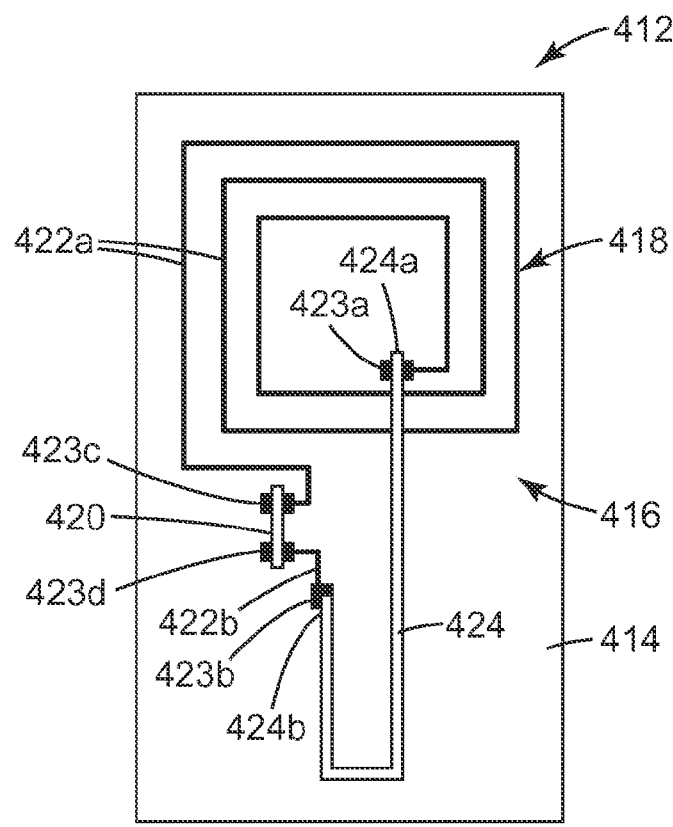
FIGS. 4, 5, 6, and 7 are schematic plan views of exemplary wetness sensors.

FIG. 4 provides a schematic view of one exemplary wetness sensor 412. The sensor 412 comprises a self-supporting substrate 414 and a tuned RF circuit 416 carried by the substrate. The substrate 414 may be a relatively small sample that has been cut from a larger piece of the same substrate material, e.g. in a converting operation on a continuous web of substrate material. Preferably, the substrate 414 is thin enough to be flexible, but thick enough to be self-supporting. The substrate 414 is preferably composed of a material that is melt-extrudable or solvent cast and capable of being cast into a flexible film. Exemplary substrate materials include films of polyethylene, polystyrene, polypropylene, and polyester. Alternatively, the sensor substrate 414 may comprise one or more materials that dissolve, swell, or otherwise degrade when contacted by the target fluid, as discussed in commonly assigned U.S. patent application Ser. No. 13/207,522, "Wetness Sensors", filed on even date herewith and incorporated herein by reference.

The sensor substrate 414 may be a unitary film, i.e., it may have a uniform composition throughout the entire space or volume of the substrate. Alternatively, the substrate may have a non-uniform composition. One type of a non-uniform composition is a stacked layered medium, or a striped medium with side-by-side lanes of differing materials, at least one of which may be degradable by the target fluid. For example, the substrate may be composed of two distinct layers of different materials, or three or more layers of materials that may all be different from each other, or that may include materials in an alternating sequence, for example. Blended materials, e.g., composed of a first material providing a continuous phase and a second material providing a dispersed phase, are also contemplated.

The wetness sensor 412 also includes an electrically conductive trace or pattern that has been applied to the substrate 414. In the embodiment of FIG. 4, the conductive pattern is divided into two sections: pattern 422a, and pattern 422b. These sections are referred to collectively as conductive pattern 422. The pattern 422 includes a spiral-shaped path that forms an inductive coil 418. The pattern 422 also includes widened areas or contact pads labeled 423a, 423b, 423c, and 423d. The pad 423a provides an inner terminus of the pattern 422 on an interior of the coil 418, and pad 423b provides an outer terminus of the pattern 422 on an exterior of the coil 418.

Pattern 422 may be applied directly to the exposed major surface of the substrate 414, or one or more intervening layers, e.g. to promote adhesion, may be included. The pattern 422 may be formed on the substrate by any suitable technique, including printing, coating, etching, electrodeposition, vapor deposition, thermographic transfer, and/or other known patterning techniques. The pattern 422 may be composed of a metal or other suitable electrically conductive materials, such as graphite and/or one or more conductive polymers, for example. Exemplary conductive materials include copper, silver, and/or nickel, but this list should not be construed as limiting. The pattern 422 preferably has a thickness that is substantially less than that of the substrate 414. In some embodiments, the pattern 422 has a thickness that is less than 1 micron, or less than 100 nanometers, for example. The pattern 422 may be so mechanically delicate that it is unable to maintain its physical integrity in the absence of a supporting substrate, i.e., substrate 414. In such cases the pattern 422, when considered by itself (separately from the supporting substrate 414), is would not be considered to be self-supporting as that term is used above. In other cases, the pattern 422 may be thicker and even self supporting, as long as the jumper 424 comprises a frangible link as discussed below.

The circuit 416 also includes a separate, discrete capacitor 420, which is connected between pads 423c and 423d of pattern 422. The capacitor 420 may be a chip capacitor or any other suitable capacitor component capable of being attached to the pads 423c, 423d as shown. Attachment may be accomplished by soldering, adhesives, or by any other suitable technique.

Finally, the circuit 416 also includes a jumper 424. The jumper 424 may provide a low impedance conductive path between inner pad 423a and outer pad 423b, with little or no resistance, capacitance, or inductance of its own. A first terminus 424a of the jumper 424 makes direct electrical contact with pad 423a, and a second terminus 424b of the jumper 424 makes direct electrical contact with pad 423b, while the jumper 424 avoids making any electrical contact with portions of the pattern 422 that it crosses over. (In FIG. 4, jumper 424 crosses over two of the loops in the coil 418 but does not make electrical contact with those loops.) In this manner, the jumper 424 has the effect of connecting the coil 418 and the capacitor 420 substantially as shown in the schematic circuit diagram of FIG. 2a. The jumper may be constructed of any suitable conductive material(s) and optional insulating material(s) that allow the jumper to provide a conductive path between pads 423a and 423b, while remaining insulated from portions of the coil 418 that it crosses over. An exemplary jumper 424 is or comprises a metal or other conductive layer disposed on an insulating polymer substrate, but other constructions are also possible. Insulating and/or conducting adhesives can also be printed on the substrate 414 or jumper 424, or otherwise be applied selectively between the jumper 424 on one side, and the substrate 414 and pattern 422 on the other side, so that the jumper 424 is held securely in place to the substrate 414 while making the necessary electrical connections and avoiding other electrical connections. Additional information on suitable jumpers is provided further below.

Significantly, the jumper 424 has associated with it a frangible link that is adapted to completely or partially fail when contacted by the target fluid. The frangible link is not separately labeled in FIG. 4 because it may comprise one (or more) of several different components associated with the jumper. For example, the frangible link may comprise a conductive or non-conductive adhesive that connects the jumper or a portion thereof to the sensor substrate, the adhesive being adapted to dissolve when contacted by water or another target fluid. The frangible link may alternatively or in addition comprise a second substrate that forms part of the jumper, the second substrate being adapted to dissolve, swell, or otherwise degrade when contacted by the target fluid. The second substrate may be self-supporting, and a conductive member disposed on the second substrate, and forming part of the jumper, is preferably not self-supporting. Exposure of the sensor tag to the target fluid can thus produce a drastic change in the physical structure of the RF circuit, and a corresponding drastic change in the operation of the RF circuit. Exemplary materials adapted to dissolve, swell, or otherwise degrade when contacted by the target fluid are discussed elsewhere herein.

The frangible link may be designed to fail when contacted by a polar target fluid such as water, or instead when contacted by a target fluid that is non-polar. Further discussion of polar and non-polar target fluids, and suitable materials adapted for use with either of these types of fluids, is provided below.

The discrete circuit elements of the circuit 416, i.e., the capacitor 420 and the jumper 424, may be attached to the substrate 414, and to the conductive pattern 422, while a web of substrate material is still intact, or after such web is slit or cut to provide the individual sensor tag 412, or a combination thereof (wherein one discrete circuit element is attached to the substrate before converting, and the other discrete circuit element is attached after converting). The discrete circuit elements (e.g., elements 420, 424) are preferably carried by the substrate and disposed on a same side of the substrate 414 as conductive pattern 422.

In an alternative embodiment, the sensor 412 may include one or two additional capacitors connected in series with the discrete capacitor 420, the additional capacitor(s) being formed at the junction of jumper terminus 424a and pad 423a, and/or at the junction of jumper terminus 424b and pad 423b. This can be accomplished by avoiding a direct electrical connection between the conductor at jumper terminus 424a and the contact pad 423a, and/or between the conductor at jumper terminus 424b and the contact pad 423b, and by instead including an insulating material (such as an insulating adhesive or film) between the appropriate jumper terminus and corresponding contact pad of the conductive pattern. By controlling the thickness of the insulating material, the size of the conductor at the jumper terminus, the size of the contact pad, and the relative position of the jumper terminus and the contact pad, a desired capacitance can be achieved at the selected junction(s).

Figure 5:
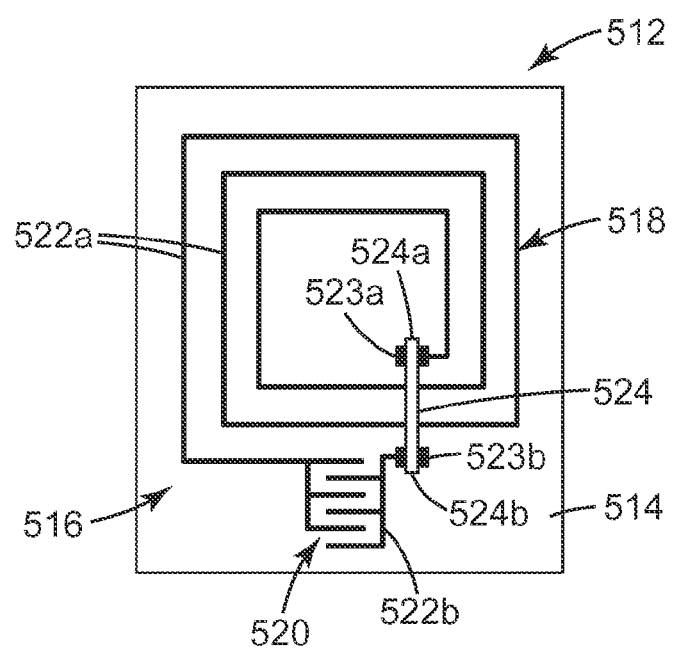

Turning now to FIG. 5, we see there a schematic view of another wetness sensor 512. Like sensor 412, the sensor 512 includes a sensor substrate 514 and a tuned RF circuit 516 carried by the substrate. Features of the substrate 414 discussed above are also applicable to the substrate 514. For example, the substrate 514 is preferably thin enough to be flexible, but thick enough to be self-supporting. Substrate 514 may be a unitary film, or it may have a non-uniform composition as discussed elsewhere herein.

The wetness sensor 512 also includes an electrically conductive pattern that has been applied to the substrate 514. Similar to the embodiment of FIG. 4, the conductive pattern is divided into two sections: pattern 522a, and pattern 522b. These sections are referred to collectively as conductive pattern 522. The pattern 522 includes a spiral-shaped path that forms an inductive coil 518. The pattern 522 also includes widened areas or contact pads at terminal portions thereof, the pads labeled 523a, 523b. The pad 523a provides an inner terminus of the pattern 522 on an interior of the coil 518, and pad 523b provides an outer terminus of the pattern 522 on an exterior of the coil 518.

Instead of the discrete capacitor 420 of FIG. 4, the sensor 512 includes an integrated capacitor 520 which may be formed by interdigitated portions of pattern 522a and trace 522b. The geometry of the interdigitated portions, such as the number of individual tines or prongs and their respective lengths and spacing, can be tailored to provide a desired amount of capacitance. Providing an integrated capacitor is advantageous by avoiding the manufacturing steps required to attach a discrete capacitor, and avoiding reliability and yield issues associated with a discrete capacitor, such as attachment failure, misalignment, detachment, and so forth.

Notwithstanding the clear design differences between pattern 522 and pattern 422, other design features discussed in connection with pattern 422 are also applicable to pattern 522. For example, the pattern 522 may be formed on the substrate 524 by any suitable technique, including printing, coating, etching, electrodeposition, vapor deposition, thermographic transfer, and/or other known patterning techniques. Further, the pattern 522 may be composed of any suitable electrically conductive materials, and may have a thickness that is substantially less than that of the substrate 514, the thickness of the pattern 522 being in some embodiments less than 1 micron, or less than 100 nanometers, for example. The pattern 522 when considered by itself may not be not self-supporting.

Similar to circuit 416, the circuit 516 also includes a jumper 524. In one embodiment, the jumper 524 provides a low impedance conductive path between inner pad 523a and outer pad 523b, with little or no resistance, capacitance, or inductance of its own. A first terminus 524a of the jumper 524 makes direct electrical contact with pad 523a, and a second terminus 524b of the jumper 524 makes direct electrical contact with pad 523b, while the jumper 524 avoids making any electrical contact with portions of the pattern 522 that it crosses over. (In FIG. 5, jumper 524 crosses over two of the loops in the coil 518 but does not make electrical contact with those loops.) In this manner, the jumper 524 has the effect of connecting the coil 518 and the capacitor 520 substantially as shown in the schematic circuit diagram of FIG. 2a.

Features of the jumper 424 discussed above are also applicable to jumper 524. In particular, the jumper 524 has associated with it a suitable frangible link that is adapted to completely or partially fail when contacted by the target fluid. Exposure of the frangible link to the target fluid produces a drastic change in the physical structure of the RF circuit 516, and a corresponding drastic change in the operation of the RF circuit 516. Exemplary frangible links are discussed in more detail elsewhere herein.

The jumper 524, which may be the only discrete circuit element of tuned RF circuit 516, or may be one of a variety of discrete circuit elements, may be attached to the substrate 514 and conductive pattern 522 while a web of substrate material is still intact, or after such web is slit or cut to provide the individual sensor tag 512. The discrete circuit element(s) including element 524 is or are preferably carried by the substrate and disposed on a same side of the substrate 514 as conductive pattern 522.

Similar to sensor 412, the sensor 512 may alternatively include one or two additional capacitors connected in series with the discrete capacitor 520, the additional capacitor(s) being formed at the junction of jumper terminus 524a and pad 523a, and/or at the junction of jumper terminus 524b and pad 523b. This can be accomplished by avoiding a direct electrical connection between the conductor at jumper terminus 524a and the contact pad 523a, and/or between the conductor at jumper terminus 524b and the contact pad 523b, and by instead including an insulating material (such as an insulating adhesive or film) between the appropriate jumper terminus and corresponding contact pad of the conductive trace. By controlling the thickness of the insulating material, the size of the conductor at the jumper terminus, the size of the contact pad, and the relative position of the jumper terminus and the contact pad, a desired capacitance can be achieved at the selected junction(s).

Figure 6:
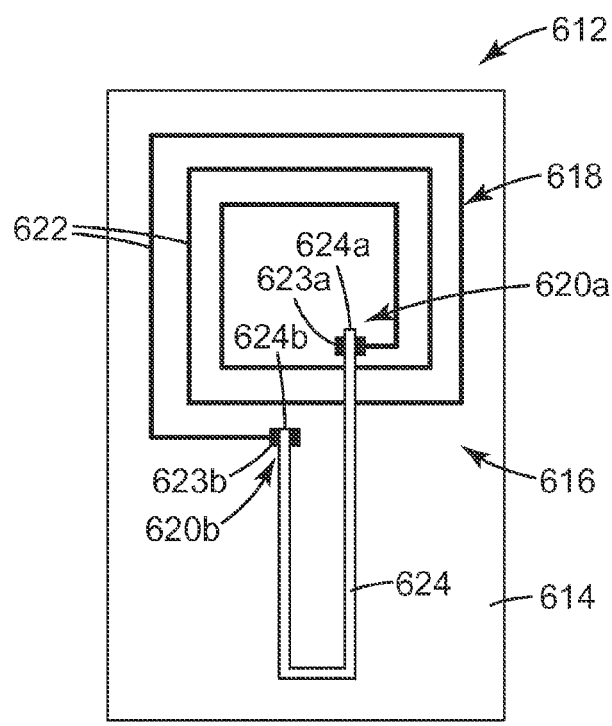

We see in FIG. 6 a schematic view of another wetness sensor 612. Like sensors 412 and 512, the sensor 612 includes a sensor substrate 614 and a tuned RF circuit 616 carried by the substrate. Features of the substrates 414, 514 discussed above are also applicable to the substrate 614. For example, the substrate 614 is preferably thin enough to be flexible, but thick enough to be self-supporting. Substrate 614 may be a unitary film, or it may have a non-uniform composition as discussed elsewhere herein.

The wetness sensor 612 also includes an electrically conductive pattern 622 that has been applied to the substrate 614. In the embodiment of FIG. 6, the conductive pattern 622 is provided in only a single contiguous section. The pattern 622 includes a spiral-shaped path that forms an inductive coil 618. The pattern 622 also includes widened areas or contact pads labeled 623a, 623b. The pad 623a provides an inner terminus of the pattern 622 on an interior of the coil 618, and pad 623b provides an outer terminus of the pattern 622 on an exterior of the coil 618.

Instead of the discrete capacitor 420 of FIG. 4, or the interdigitated capacitor 520 of FIG. 5, the sensor 612 includes capacitors 620a and 620b that are formed at the junctions of the pads 623a, 623b with terminuses of a jumper 624. These capacitors 620a, 620b are described further below in connection with the jumper 624.

Notwithstanding the clear design differences between pattern 622 and the patterns 422, 522, other design features discussed in connection with patterns 422, 522 are also applicable to pattern 622. For example, the pattern 622 may be formed on the substrate 614 by any suitable technique, including printing, coating, etching, electrodeposition, vapor deposition, thermographic transfer, and/or other known patterning techniques. Further, the pattern 622 may be composed of any suitable electrically conductive materials, and may have a thickness that is substantially less than that of the substrate 614, the thickness of the pattern 622 being in some embodiments less than 1 micron, or less than 100 nanometers, for example. The pattern 622 when considered by itself may not be not self-supporting.

As already mentioned, circuit 616 includes jumper 624. In one embodiment, the jumper 624 provides capacitive coupling between the contact pads 623a, 623b and terminuses 624a, 624b respectively so as to provide distinct capacitors 620a, 620b, the jumper 624 also providing a low impedance conductive path along the jumper between the terminuses 624a, 624b. Capacitive coupling between a given terminus of the jumper 624 and its corresponding contact pad of the pattern 622 can be accomplished by including an insulating material (such as an insulating adhesive or film) between the jumper terminus and the contact pad. By controlling the thickness of the insulating material, the size of the conductor at the jumper terminus, the size of the contact pad, and the relative position of the jumper terminus and the contact pad, a desired capacitance 620a, 620b can be achieved at the respective junction. The jumper 624 avoids making any electrical contact with portions of the pattern 622 that it crosses over. (In FIG. 6, jumper 624 crosses over two of the loops in the coil 618 but does not make electrical contact with those loops. Furthermore, capacitive coupling between the jumper and such portions of the pattern 622 is preferably negligible in comparison to capacitors 620a, 620b.) In this manner, the jumper 624 has the effect of providing two capacitors connected to the coil 618 substantially as shown in the schematic circuit diagram of FIG. 2b.

Features of jumpers 424, 524 discussed above are also applicable to jumper 624. In particular, the jumper 624 has associated with it a suitable frangible link that is adapted to completely or partially fail when contacted by the target fluid. Exposure of the frangible link to the target fluid produces a drastic change in the physical structure of the RF circuit 616, and a corresponding drastic change in the operation of the RF circuit 616. The frangible link may be provided by selecting the insulating material used in one or both of capacitors 620a, 620b to be a material that dissolves, swells, or otherwise degrades when exposed to the target fluid. Contact with the target fluid may then render one or both of the capacitors 620a, 620b wholly or partially inoperative, for example. Further information on exemplary frangible links is provided elsewhere herein.

The jumper 624, which may be the only discrete circuit element of tuned RF circuit 616, may be attached to the substrate 614 and conductive pattern 622 while a web of substrate material is still intact, or after such web is slit or cut to provide the individual sensor tag 612. The discrete circuit element 624 is preferably carried by the substrate and disposed on a same side of the substrate 614 as conductive pattern 622.

In an alternative embodiment, one of the capacitors 620a, 620b may be eliminated by providing a direct electrical connection between the associated terminus of the jumper 624 and its corresponding contact pad of the conductive pattern 622. For example, capacitor 620a may be eliminated by providing a direct electrical connection between terminus 624a of the jumper and the contact pad 623a. Alternatively, capacitor 620b may be eliminated by providing a direct electrical connection between terminus 624b of the jumper and the contact pad 623b. In either case the result is a tuned RF circuit in which the (sole) remaining capacitor is connected with an inductor as shown in the circuit diagram of FIG. 2a. In these alternative embodiments, the frangible link may alternatively or in addition be directed to the portion of the jumper 624 that makes a direct electrical connection with the corresponding contact pad. For example, a conductive adhesive may be used to physically and electrically connect a terminus of the jumper 624 with its corresponding contact pad of the conductive pattern 622, and the conductive adhesive may be adapted to dissolve, swell, or otherwise degrade when contacted by the target fluid.

Figure 7:
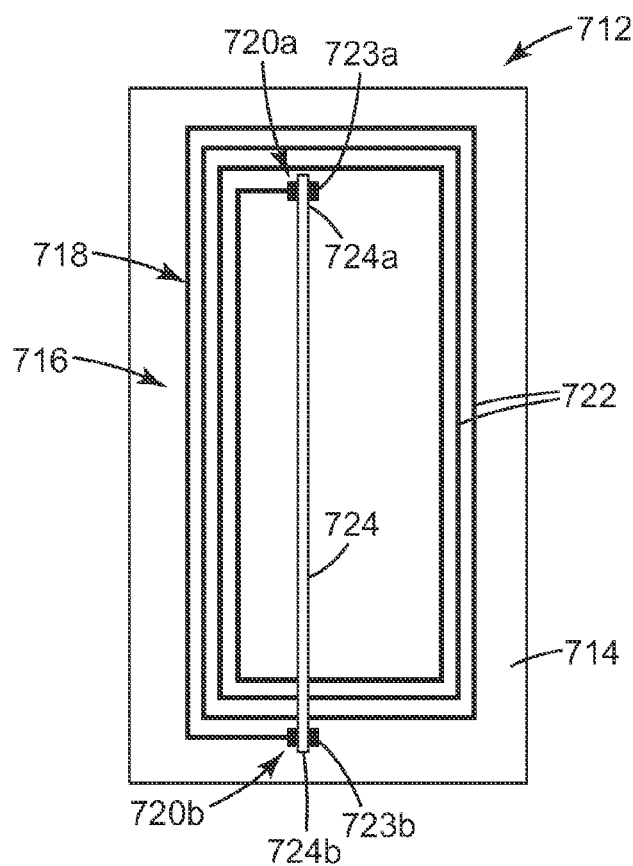

FIG. 7 depicts a wetness sensor 712 that is similar in many ways to sensor 612 of FIG. 6, but with a different aspect ratio of the coil and with a straight jumper rather than a U-shaped jumper. Like sensors 412, 512, and 612, the sensor 712 includes a sensor substrate 714 and a tuned RF circuit 716 carried by the substrate. Features of the substrates 414, 514, and 614 discussed above are also applicable to the substrate 714. For example, the substrate 714 is preferably thin enough to be flexible, but thick enough to be self-supporting. Substrate 714 may be a unitary film, or it may have a non-uniform composition.

The wetness sensor 712 also includes an electrically conductive pattern 722 that has been applied to the substrate 714. In the embodiment of FIG. 7, the conductive pattern 722 is provided in only a single contiguous section. The pattern 722 includes a spiral-shaped path that forms an inductive coil 718. The pattern 722 also includes widened areas or contact pads labeled 723a, 723b. The pad 723a provides an inner terminus of the pattern 722 on an interior of the coil 718, and pad 723b provides an outer terminus of the pattern 722 on an exterior of the coil 718.

Similar to sensor 612, the sensor 712 includes capacitors 720a and 720b that are formed at the junctions of the pads 723a, 723b with terminuses of a jumper 724. These capacitors 720a, 720b are described further below in connection with the jumper 724.

Notwithstanding the clear design differences between conductive pattern 722 and the conductive patterns 422, 522, and 622, other design features discussed in connection with patterns 422, 522, and 622 are also applicable to pattern 722. For example, the pattern 722 may be formed on the substrate 714 by any suitable technique, including printing, coating, etching, electrodeposition, vapor deposition, thermographic transfer, and/or other known patterning techniques. Further, the pattern 722 may be composed of any suitable electrically conductive materials, and may have a thickness that is substantially less than that of the substrate 714, the thickness of the pattern 722 being in some embodiments less than 1 micron, or less than 100 nanometers, for example. The pattern 722 when considered by itself may not be self-supporting.

Circuit 716 includes jumper 724. In one embodiment, the jumper 724 provides capacitive coupling between the contact pads 723a, 723b and terminuses 724a, 724b respectively so as to provide distinct capacitors 720a, 720b, the jumper 724 also providing a low impedance conductive path along the jumper between the terminuses 724a, 724b. Capacitive coupling between a given terminus of the jumper 724 and its corresponding contact pad of the pattern 722 can be accomplished by including an insulating material (such as an insulating adhesive or film) between the jumper terminus and the contact pad. By controlling the thickness of the insulating material, the size of the conductor at the jumper terminus, the size of the contact pad, and the relative position of the jumper terminus and the contact pad, a desired capacitance 720a, 720b can be achieved at the respective junction. The jumper 724 avoids making any electrical contact with portions of the pattern 722 that it crosses over. (In FIG. 7, jumper 724 crosses over three of the loops in the coil 718 but does not make electrical contact with those loops. Furthermore, capacitive coupling between the jumper and such portions of the pattern 722 is preferably negligible in comparison to capacitors 720a, 720b.) In this manner, the jumper 724 has the effect of providing two capacitors connected in series to the coil 718 substantially as shown in the schematic circuit diagram of FIG. 2b.

Features of jumpers 424, 524, 624 discussed above are also applicable to jumper 724. In particular, the jumper 724 has associated with it a suitable frangible link that is adapted to completely or partially fail when contacted by the target fluid. Exposure of the frangible link to the target fluid produces a drastic change in the physical structure of the RF circuit 716, and a corresponding drastic change in the operation of the RF circuit 716. The frangible link may be provided by selecting the insulating material used in one or both of capacitors 720a, 720b to be a material that dissolves, swells, or otherwise degrades when exposed to the target fluid. Contact with the target fluid may then render one or both of the capacitors 720a, 720b wholly or partially inoperative, for example. Further information on exemplary frangible links is provided elsewhere herein.

The jumper 724, which may be the only discrete circuit element of tuned RF circuit 716, may be attached to the substrate 714 and conductive pattern 722 while a web of substrate material is still intact, or after such web is slit or cut to provide the individual sensor tag 712. The discrete circuit element is preferably carried by the substrate and disposed on a same side of the substrate 714 as conductive pattern 722.

In an alternative embodiment, one of the capacitors 720a, 720b may be eliminated by providing a direct electrical connection between the associated terminus of the jumper 724 and its corresponding contact pad of the conductive pattern 722. For example, capacitor 720a may be eliminated by providing a direct electrical connection between terminus 724a of the jumper and the contact pad 723a. Alternatively, capacitor 720b may be eliminated by providing a direct electrical connection between terminus 724b of the jumper and the contact pad 723b. In either case the result is a tuned RF circuit in which the (sole) remaining capacitor is connected with an inductor, as shown in the circuit diagram of FIG. 2a. In these alternative embodiments, the frangible link may alternatively or in addition be directed to the portion of the jumper 724 that makes a direct electrical connection with the corresponding contact pad. For example, a conductive adhesive may be used to physically and electrically connect a terminus of the jumper 724 with its corresponding contact pad of the conductive pattern 722, and the conductive adhesive may be adapted to dissolve, swell, or otherwise degrade when contacted by the target fluid.

The reader will understand that the embodiments described in connection with FIGS. 4-7 are merely exemplary and are not intended to be limiting. Features of any given described sensor are intended to be applicable to other sensors, to the extent possible. For example, discrete or integrated capacitors described in connection with FIGS. 4 and 5 may also be incorporated into the circuits of FIGS. 6 and 7. Aspect ratios of the sensors and/or of the sensor coils can be adapted as desired, compare e.g. aspect ratios of FIG. 5 with those of FIG. 7. Furthermore, the sensors can be modified by incorporation of other design features mentioned elsewhere herein, e.g., incorporation of an RFID integrated circuit chip into a given tuned RF circuit.

Figure 8:
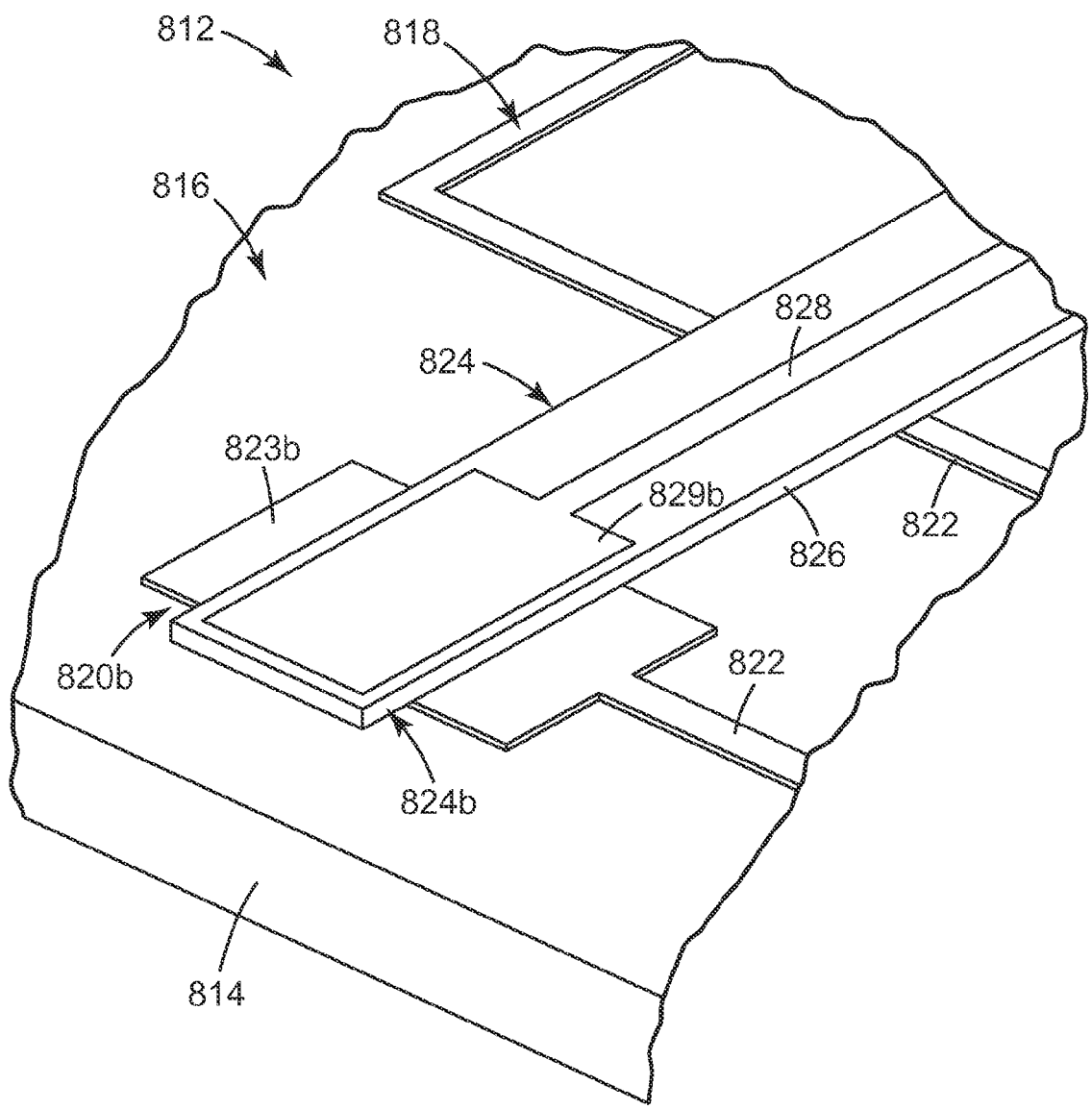
FIG. 8 is a schematic perspective view of a detail of an exemplary wetness sensor.

FIG. 8 is a schematic view of a portion of an exemplary wetness sensor 812 or sensor tag that shows additional detail with regard to a jumper attached to the substrate of the sensor. Sensor 812 thus includes a sensor substrate 814, to which has been applied a conductive pattern 822. The substrate 814 is preferably self-supporting, and it carries a tuned RF circuit 816, of which the conductive pattern 822 is a part. The pattern 822 may not be self-supporting. Pattern 822 may include at least an inductive coil 818 and a contact pad 823b.

A jumper 824 is attached to the substrate and/or to a portion of the conductive pattern, such as with one or more adhesives (not shown) or by other suitable means. The jumper, which may be or comprise a layer of metal or other conductive material disposed on an electrically insulating substrate such as a layer of polymer material, couples directly or capacitively to the contact pad 823b of the pattern 822. Furthermore, the jumper preferably avoids both direct contact and significant capacitive coupling to portions of the pattern 822 that it crosses over. This can be done, in some embodiments, by providing the jumper with a conductor whose transverse dimension or width is greater at a terminus of the jumper compared to portions of the jumper that cross over the previously mentioned portions of the pattern 822. The widened conductor may form a tab at the jumper terminus, the tab preferably being aligned with or positioned to correspond to a contact pad 823b of the conductive pattern 822, as shown in FIG. 8. Such alignment or positioning enhances capacitive coupling between the jumper terminus and the contact pad, or, if direct electrical contact is desired, simplifies the process of making direct electrical contact therebetween.

In the embodiment of FIG. 8, the jumper 824 comprises a jumper substrate 826 to which a conductor 828 has been applied, the conductor 828 being widened at the terminus 824b to provide a tab 829b. The jumper substrate 826 may, for example, comprise a thin flexible film or other suitable component. The jumper substrate 826 of FIG. 8 is depicted as being electrically insulative, such that the tab 829b and pad 823b form a capacitor 820b.

The conductor 828 (including tab 829b) may be applied directly to the exposed major surface of the substrate 826, or one or more intervening layers, e.g. to promote adhesion, may be included. The conductor 828 may be made by printing, coating, etching, electrodeposition, vapor deposition, thermographic transfer, and/or other known techniques, and may be composed of the same material as conductive pattern 822, or, in some embodiments, of a different material. Thus, for example, the conductor 828 of the jumper may be made of a metal or other suitable electrically conductive material, such as graphite and/or one or more conductive polymers, for example. Exemplary conductive materials include copper, silver, and/or nickel, but this list should not be construed as limiting. The conductor 828 preferably has a thickness that is substantially less than that of the substrate 826. In some embodiments, the conductor 828 has a thickness that is less than 1 micron, or less than 100 nanometers, for example. Preferably, the conductor 828 is so mechanically delicate that it is unable to maintain its physical integrity in the absence of a supporting substrate, i.e., substrate 826. Conductor 828, when considered by itself (separately from the supporting substrate 826), is thus preferably not self-supporting as that term is used herein. Consequently, if some or all of the substrate 826 dissolves in the presence of the target fluid, the conductor 828 (including tab 829b) may lose its mechanical integrity, giving rise to a drastic change in the operation of the RF circuit 816.

As discussed above, the jumper has a frangible link associated with it. The frangible link is not labeled in FIG. 8 because it may comprise one or more of several different components associated with the jumper. The frangible link may, for example, be or comprise the jumper substrate 826, provided that that substrate is composed of a material that dissolves, swells, or otherwise degrades when contacted by the target fluid. The jumper substrate 826 in such cases is preferably self-supporting, and the conductor 828 is preferably not self-supporting. In this way, when water or another target fluid contacts the construction, the physical structure of conductor 828 (including tab 829b) can change drastically, particularly if the jumper substrate 826, which originally provided the mechanical support for conductor 828, completely or partially dissolves.

For aqueous sensors, suitable materials useable for the jumper substrate 826 may be selected from any of the known natural or synthetic water-soluble or water-dispersible materials. Preferred substrate materials are also melt-extrudable and capable of being cast into flexible films. An exemplary film-forming polymer or oligomer substrate material is polyvinyl alcohol (PVA). PVA is a polar material, and it substantially dissolves and/or swells when exposed to water or other polar liquids, including aqueous human body fluids such as urine or blood. Polymers of PVAs may be prepared from polyvinyl acetate and can be commercially obtained in a variety of molecular weights and hydrolysis levels. Alternative dissolvable or degradable substrate materials include, but are not limited to: frangible papers such as tissue paper or newsprint; vegetable natural polymers such as alginic acid and alginic acid derivated polymers, arabinogalactan, cellulose derivatives including but not limited to hydroxyethylcellulose, hydroxypropylcellulose, hydroxylpropyl methylcellulose, methylcellulose, carboxymethylcellulose, starch, and starch derivitives; microorganism-derived natural polymers such as polysaccharides, polymers derived from animals including gelatin, collagen, mucopolysaccharides and the like; plyoxyalkylenes; polymers and copolymers derived from ethnically unsaturated monomers including, but not limited to vinylic monomers, acrylates and methacrylates, acrylamides and methacrylamides, and the like; polyethyleneimines; polylactic acid; polyglycolic acid; and mixtures including one or more of the forgoing. Additional suitable substrate materials include polyethylene oxide or polyethylene glycol, pectin, pullulan, and carbopol-based polymer films. Still other suitable substrate materials may be selected from the materials disclosed in PCT publication WO 02/092049 (Godbey et al.), "System for Delivering Cosmetics and Pharmaceuticals", incorporated herein by reference. As disclosed in that document, plasticizers can be used to reduce the brittleness of the film, thereby making the film tougher, more conformable, and generally improving its handling properties. Another suitable substrate material is Water-Soluable Wave Solder Tape #5414 available from 3M Company, which is a tape having a PVA film backing, a synthetic water soluble adhesive, and a Kraft paper liner.

In some cases, the wetness sensor may be designed to detect a target fluid other than water, or may even detect a fluid other than a polar liquid, e.g., a non-polar liquid derived from petroleum based products such as gasoline, kerosene, hexane, heptane, toluene, and other aromatic, straight chained, or branched hydrocarbons or mixtures thereof. For a wetness sensor designed to detect a non-polar liquid, the jumper substrate may preferably be composed of a non-polar material. For example, polystyrene is a non-polar material that may be used as, or included in, a jumper substrate and will dissolve, swell, or otherwise degrade when contacted by a non-polar target fluid. Other exemplary substrates that will degrade with non-polar target fluids include those made from ABS, EPDM, PVC, polypropylene, and other non-polar materials that preferably have little or no crosslinking, plasticizers or stabilizers.

The jumper substrate 826 may be a unitary film, i.e., it may have a uniform composition throughout the entire space or volume of the substrate. Alternatively, the substrate may have a non-uniform composition. One type of a non-uniform composition is a stacked layered medium, or striped medium with side-by-side lanes of differing materials, at least one of which is degradable by the target fluid. For example, the substrate may be composed of two distinct layers of different materials, or three or more layers of materials that may all be different from each other, or that may include materials in an alternating sequence, for example. Blended materials, e.g., composed of a first material providing a continuous phase and a second material providing a dispersed phase, are also contemplated. In cases where the sensor substrate is composed of a plurality of distinct materials, whether layered, blended, coextruded, striped, or otherwise, one, some, or all of the plurality of materials may be soluble, or may swell, or may otherwise degrade, for example, in the presence of the target fluid.

In cases where a direct electrical connection is desired between the jumper 824 and the pattern 822 at the terminus 824*b*, a volume of conductive adhesive (not shown) may, for example, be applied in an amount sufficient to cover both the tab 829*b* and the exposed portions of pad 823*b*, such adhesive not only making a direct electrical connection between the tab and the pad, but also mechanically bonding the terminus 824*b* of the jumper 824 to the substrate 814 through pad 823*b*. FIG. 8 shows the jumper substrate 826 extending fully under tab 829*b*, however to make electrical contact between the pad 823*b* and the tab 829*b* at terminus 824*b*, the conductive tab 829*b* can extend beyond the jumper substrate 826 so that there is no insulating film between tab 829*b* and pad 823*b*. Additionally or alternatively, an adhesive may be provided between the jumper 824 and the sensor substrate 814/conductive pattern 822 to bond the jumper 824 to the substrate.

In such cases, the frangible link may additionally or alternatively include one or more of the conductive or non-conductive adhesives used to mechanically and/or electrically couple the jumper to other elements of the sensor 812. The one or more adhesives forming the frangible link may thus be tailored to dissolve, swell, or otherwise degrade when contacted by the target fluid. Exemplary adhesives in this regard include water soluble or water dispersible adhesives such as those described in publications US 2002/0187181 (Godbey et al.) and US 2010/0272784 (Kantner et al.) and water soluble electrically conductive adhesives such as those described in U.S. Pat. No. 4,848,353 (Engel), the contents of which are incorporated herein by reference. Exposure of the sensor tag to the target fluid may result in such adhesive(s) completely or partially dissolving, for example, producing a drastic change in the physical structure of the jumper conductor, and a corresponding drastic change in the operation of the RF circuit.

The jumper arrangements discussed in connection with FIG. 8 may be utilized in any of the sensor embodiments discussed herein, as appropriate for the particular embodiment or portion thereof.

Figure 9A:
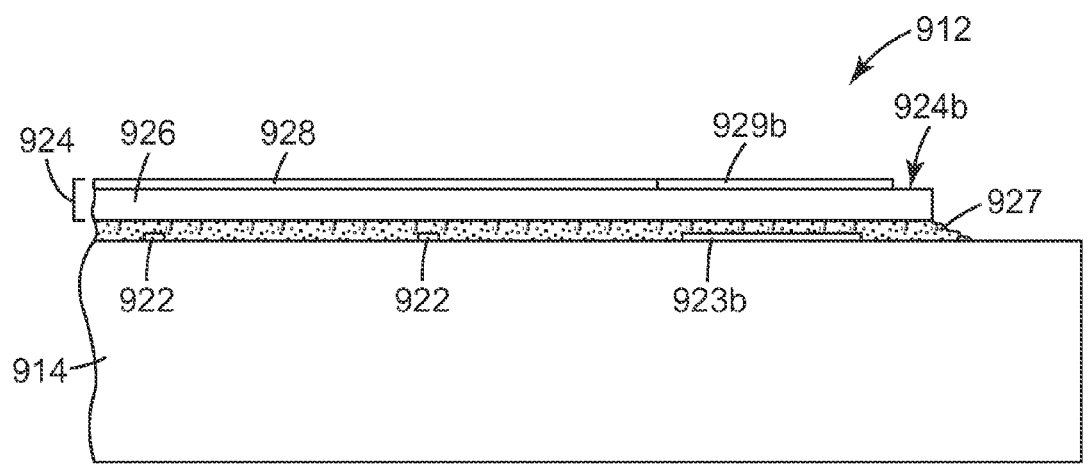
FIG. 9a is a schematic side or cross-sectional view of a portion of a wetness sensor.

FIG. 9*a* is a schematic view of a portion of a wetness sensor 912 or sensor tag that also shows detail with regard to a jumper attached to the substrate of the sensor, where the jumper may be or comprise a layer of metal or other conductive material disposed on an insulating polymer substrate. Sensor 912 thus includes a sensor substrate 914, to which has been applied a conductive pattern 922. The pattern 922 is widened locally to provide a pad 923*b*. The substrate 914 is preferably self-supporting. The substrate 914 also preferably carries a tuned RF circuit, of which the conductive pattern 922 is a part. The pattern 922 may not be self-supporting. Pattern 922 may include at least an inductive coil and the contact pad 923*b*.

A jumper 924 is shown attached to the substrate 914 via an adhesive layer 927. The adhesive layer 927 as shown is electrically non-conductive; otherwise, if the layer 927 were conductive, it would cause short-circuiting between the different portions of the conductive pattern 922 that it contacts. Representative non-conductive adhesive materials may be or include, for example, silicone, acrylate, urethane, tackified natural or synthetic rubber, or other adhesives that do not exhibit conductive properties in the frequency ranges described for this system. The jumper 924 includes a conductor 928 disposed on a jumper substrate 926. The conductor 928 may have a given limited transverse dimension or width along the length of the jumper, but may be expanded or widened to form a tab 929*b* at a terminus 924*b* of the jumper.

The widened tab 929*b* forms a capacitor with pad 923*b*, the value of the capacitance depending on the dielectric properties and thicknesses of the adhesive layer 927 and of the jumper substrate 926, and on the relative geometry of the tab 929*b* and pad 923*b*. The jumper substrate 926 is assumed to be electrically insulative, but in some embodiments it may be electrically conductive, in which case the separate conductor 928 may be omitted from the jumper as redundant.

The jumper 924 may include a frangible link if, for example, the jumper substrate 926 is or includes a material adapted to dissolve, swell, or otherwise degrade when contacted by the target fluid. Exemplary substrate materials suitable for this purpose are discussed above. Alternatively or in addition, any of the adhesive materials discussed above may be formulated to dissolve, swell, or otherwise degrade when contacted by the target fluid. Exemplary non-conductive adhesive materials may include, for example, a lightly crosslinked or uncrosslinked polar polymer and a plasticizer in an amount sufficient to provide a degree of pressure sensitive tack. Suitable adhesives may or may not include water. Such an adhesive provides good adhesion and rapid water-solubility without negatively affecting the film to which it is applied. Polymers suitable for use in the adhesive include, but are not limited to, poly(ethylene oxide); natural and synthetic polysaccharides and their derivatives; and homopolymers and copolymers of ethylenically unsaturated hydrophilic monomers including ethylenic unsaturated carboxylic acids having 3 to 8 carbon atoms such as (meth)acrylic acid and salts thereof as well as polymers derived from polymerization and subsequent hydrolysis of unsaturated anhydrides such as maleic anhydride and itaconic anhydride; acrylamide, N-vinyl pyrrolidone, hydroxyethyl(meth)acrylate, acylamidopropane sulfonic acid and salts thereof; methyl vinyl ether; ethyl vinyl ether; and polymers having ammonium functionality derived from reaction of amine containing monomers with alkylating agents or protic acids, for example N,N'-dimethylaminoethyl(meth)acrylate and its derivatives, and vinyl pyridine. Polymers suitable for use in the adhesive may be an uncrosslinked polymer or mixture of polymers with an overall number average molecular weight between 10,000 and 100,000 daltons. Such polymers provide a good balance of cohesive strength and water-solubility. The adhesive composition may include the polymer in a relative amount of from about 10 to about 60 weight percent of the adhesive composition. Certain embodiments may include an adhesive composition including from about 20 to about 50 weight percent polymer. Adhesive compositions containing this level of hydrophilic polymeric matrix have a desirable balance of tack, softness, adhesiveness, and cohesive strength. The adhesive composition may further include a plasticizer that includes from about 10 to about 80 weight percent (relative to the total weight of the adhesive) polar organic compound and about 0 to 60 weight percent water. All of these weight percents are based on the total weight of the entire adhesive composition. Suitable compounds for use in the plasticizer include, but are not limited to, monohydric alcohols and polyhydric alcohols. Low molecular weight polyoxyethylenes (average molecular weight up to 600 daltons), glycerol, monomethoxypolyoxyethylene and propanediol are suitable because they give good adhesive performance. The adhesive composition may contain the plasticizer in an amount up to about 80 weight percent and water in an amount up to about 60 weight percent. Certain embodiments may include plasticizer from about 10 to about 50 percent by weight and water up to about 10 percent by weight. Such adhesives generally have a good balance of pressure sensitive adhesive performance while maintaining good water solubility. An exemplary adhesive includes a polymer of crosslinked polyvinyl pyrrolidone, a glycol plasticizer and optionally water. Other exemplary non-conducting adhesives include poly(2-ethyl-2-oxazoline), and a PSA comprising a homogeneous blend comprising (a) a polymer selected from the group consisting of N-vinyl caprolactam homopolymers, N-vinyl pyrrolidone copolymers, and mixtures thereof and (b) a non-volatile plasticizer comprising a monohydric or polyhydric alcohol having hydrophilic-lipophilic balance of about 2 to about 1.

Exemplary conductive adhesive materials include, for example, crosslinked swellable polymeric matrices that can be fully swelled without dissolving. When these crosslinked materials are swelled with water they are called hydrogels. Exemplary adhesives are shown in many patents, including U.S. Pat. No. 4,274,420 (Hymes), U.S. Pat. No. 4,352,359 (Larimore et al.), U.S. Pat. No. 4,524,087 (Engel), U.S. Pat. No. 4,539,996 (Engel), and U.S. Pat. No. 4,554,924 (Engel). The '087 and '996 Engel patents disclose an electrically-conductive adhesive formed by an essentially solventless free radical polymerization of an adhesive precursor having a polyhydric alcohol, at least one ionic monomer, a crosslinker, and an initiator. Non-ionic comonomers may be included. Ionic monomers listed are salts of alpha, beta-unsaturated carboxylic acids such as potassium and sodium acrylate and sodium methacrylate. Non-ionic comonomers listed are acrylic acid, methacrylic acid, and hydroxyethyl methacrylate. The '924 Engel patent discloses a conductive adhesive formed by an essentially solventless free radical polymerization of an adhesive precursor having a polyhydric alcohol, at least one non-ionic monomer, an initiator, a crosslinker, and an ionizable salt present in an amount sufficient to render the composition conductive. Non-ionic monomers shown are acrylic acid, methacrylic acid, hydroxyethyl methacrylate, and N-vinylpyrrolidone. Another conductive adhesive is disclosed in U.K. Patent Application GB 2,115,431 (Sieverding). That publication describes adhesives formed by dissolving or dispersing polymers in a plasticizing liquid and subjecting the mixture to radiation. The conductive adhesive described is prepared from polyvinylpyrrolidone, polyethylene glycol, magnesium acetate, methyl paraben, propyl paraben, FD&C Blue #2 and water. An electrically-conductive adhesive sold under the trademark Polyhesiveä (Valleylab, Inc., Boulder, Colo.) is believed to be made according to the disclosure of the GB 2,115,431 publication. Another suitable adhesive is Z-axis Electrically Conductive Double Sided Tape, commercially available from the 3M Company, St. Paul, Minn., USA.

A class of adhesives that can be dispersed or dissolved in polar solutions including water is the class of repulpable adhesives. They are generally not crosslinked. One such repulpable adhesive is made with a comonomer of butyl acrylate and methyl diethanol ammonium acrylate. Ionic species may be soluble in these adhesives to make them conductive. An exemplary adhesive is made from a conformable, cohesive, adhesive copolymer matrix formed by free radical polymerizing an adhesive precursor comprising a carboxylic acid as a water-soluble hydrogen bond donating monomer, N-vinyl pyrrolidone as a water-soluble hydrogen bond accepting monomer, and a polymerization initiator, with a plasticizing, electrically-conductive solution having from about 0 to 98% by weight water-soluble, polar organic compound, about 2 to 100% by weight water, and about 0 to 12% by weight water-soluble salt such as a halide. The chloride, iodide, and bromide salts of sodium and potassium may conveniently be used. Particularly preferred is potassium chloride. The plasticizing electrically-conductive solution is "electrically-conductive" if it contains polar or ionic species effective to provide sufficient electrical conductivity in the final composition for the intended application. The ratio of soluble polar organic compound to water and the concentration of salt may be varied depending on the rheological and electrical properties desired.

Figure 9B:
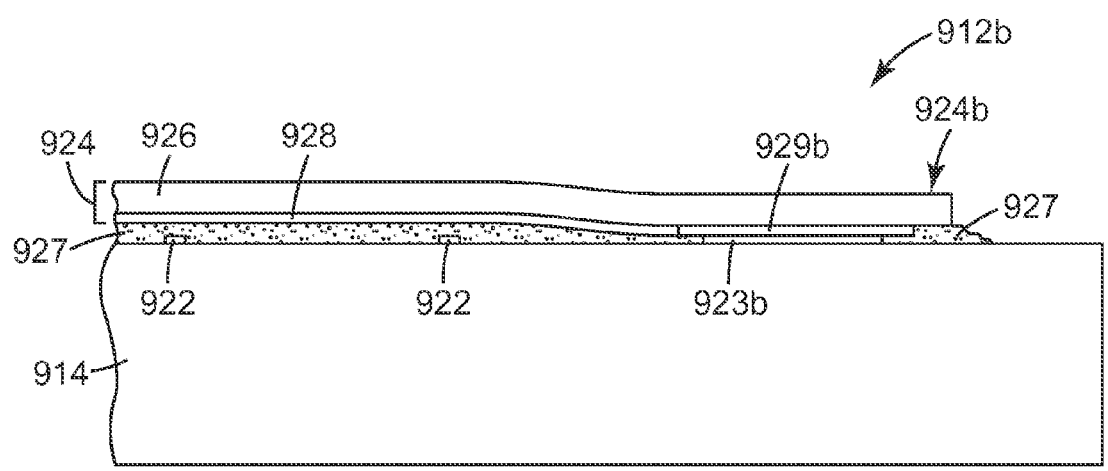
FIG. 9b is a schematic side or cross-sectional view of a portion of another wetness sensor.

FIG. 9b is a schematic view of a portion of another wetness sensor 912b, the figure again showing detail with regard to a jumper where the jumper 924 is or comprises a metal or other conductive layer disposed on an insulating polymer substrate 926. Sensor 912b is similar in many respects to sensor 912 of FIG. 9a, and like components are labeled with like reference numerals, such components needing no further explanation beyond that provided above. Sensor 912b differs from sensor 912 in that the jumper 924 has been flipped over such that its orientation relative to sensor substrate 914 and conductive trace 922 is reversed, compared to its orientation in FIG. 9a. Furthermore, increased pressure has been applied selectively in the vicinity of the jumper terminus 924b so as to force the electrically insulative adhesive out of the region between tab 929b and pad 923b, such that direct electrical contact is made between the tab 929b and pad 923b. Such increased pressure has not been applied to the remaining portions of the jumper shown in the figure, so that the jumper 924 avoids direct electrical contact and significant capacitive coupling to the other portions of the conductive pattern 922 shown in the figure. In some cases, a second terminus (not shown in FIG. 9b) at an end of the jumper 924 opposite terminus 924b may likewise provide direct electrical contact between a similar tab of the conductor 928 and a similar pad of the conductive pattern 922, such that the jumper 924 provides direct electrical contact with the pattern 922 at both ends of the jumper. In other cases, increased pressure may not be applied to the second terminus of the jumper 924, such that insulative adhesive remains disposed between the second tab of the conductor 928 and the second pad of the pattern 922, and such that the jumper 924 provides direct electrical contact at the end or terminus of the jumper shown in FIG. 9b, but provides capacitive coupling at the opposite or second end or terminus of the jumper 924.

The jumper 924 of FIG. 9b may include a frangible link if, for example, the jumper substrate 926 is or includes a material adapted to dissolve, swell, or otherwise degrade when contacted by the target fluid. Alternatively or in addition, the adhesive layer 927 may be formulated to dissolve, swell, or otherwise degrade when contacted by the target fluid.

Figure 9C:
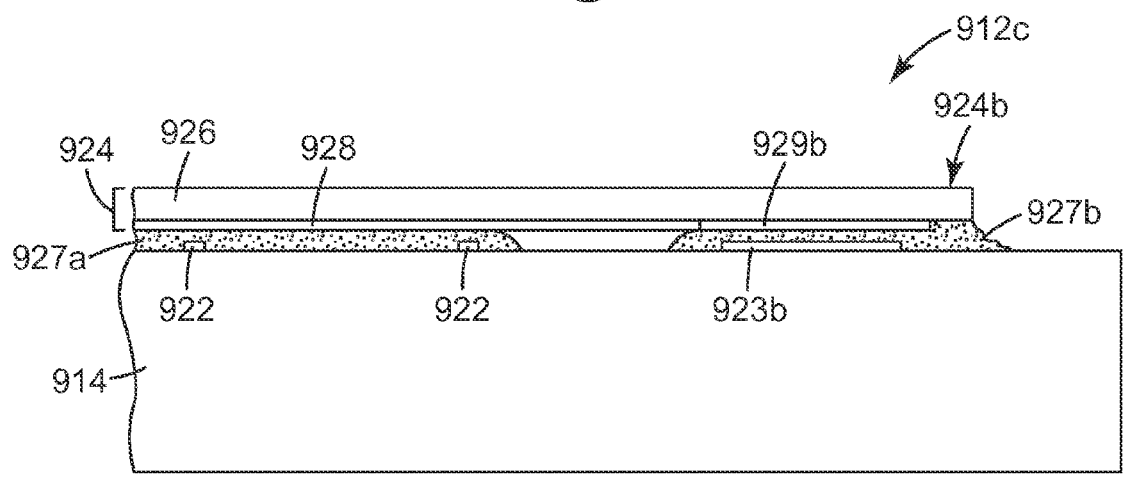
FIG. 9c is a schematic side or cross-sectional view of a portion of yet another wetness sensor.

FIG. 9c depicts wetness sensor 912c that combines aspects of FIGS. 9a and 9b. Like FIG. 9a, the tab 929b of jumper 924 is capacitively coupled to the contact pad 923b. But like FIG. 9b, jumper 924 is oriented "downwardly", i.e., with the conductor 928 disposed between the sensor substrate 914 and the jumper substrate 926. The extended adhesive layer 927 of FIG. 9a is replaced in 9c with an adhesive layer 927b that is more localized in the vicinity of the capacitor formed between tab 929b and pad 923b, and that does not extend along the entire length of the jumper 924. Another insulating layer 927a is provided beneath other portions of the jumper 924. The layer 927a at least covers the portions of conductive pattern 922 that lie beneath the jumper 924 so as to prevent the conductor 928 from making electrical contact with the conductive pattern 922. Unlike the adhesive layer 927b, the insulating layer 927a preferably provides little or no actual adhesion to the conductor 928. That is, although the insulating layer 927a preferably bonds to the sensor substrate 914, and optionally also to the conductive pattern 922, it does not substantially bond to the conductor 928. The capacitance formed between tab 929b and pad 923b is a strong function of the thickness and dielectric properties of adhesive layer 927b, but unlike the embodiment of FIG. 9a, it is substantially insensitive to the thickness and dielectric properties of jumper substrate 926.

Preferably, the adhesive layer 927b of jumper 912c is made to be relatively insensitive to the target fluid, e.g., it may neither dissolve nor swell, nor otherwise degrade, to any significant degree, when contacted by the target fluid, but the jumper substrate 926 is preferably selected to dissolve (or otherwise swell or degrade) when contacted by the target fluid. Further, the jumper substrate 926 is preferably made to be self-supporting, but the conductor 928 is not. When such an article is contacted by the target fluid, the jumper substrate 926 may dissolve, for example, while the remaining components of the article may not dissolve. However, in the absence of the (self-supporting) jumper substrate 926, the portion of the (non-self-supporting) conductor 928 that is not bonded in place by the adhesive layer 927b will be free to break apart or otherwise disintegrate, even though the tab 929b may remain intact due to the bonding action of the adhesive layer 927b. The capacitor formed by tab 929b and pad 923b may thus remain intact after contact with the target fluid, while the conductive path that connects the tab 929b with a tab on the opposite end of the jumper may disintegrate or fail, leading, e.g., to a substantial open circuit condition for the tuned RF circuit, and rendering the RF circuit substantially inoperative. An advantage of this design approach compared to embodiments that incorporate a dissolvable or swellable material between the plates of the capacitor may be better sensor-to-sensor repeatability in resonance characteristics of the RF circuit, and/or better stability of the resonance characteristic of a given sensor in the presence of high humidity, for example.

In one non-limiting but exemplary embodiment of FIG. 9c, the substrate 914 may be or comprise a 2 mil (51 micron) thick film of polyester, the conductive pattern 922 (including contact pad 923b) may be or comprise a 1.4 mil (35 micron) thick layer of copper, the jumper substrate 926 may be or comprise a 2 mil (51 micron) thick layer of PVA, the conductor 928 (including tab 929b) may be or comprise a 40 to 150 nanometer thick film of silver, the adhesive layer 927b may be or comprise about a 2 mil (51 micron) thick layer of z-axis electrically conductive double-sided tape, and the insulating layer 927a may be or comprise about a 2 mil (51 micron) micron thick layer of electrically non-conductive acrylic adhesive bonding tape.

The jumper arrangements discussed in connection with FIGS. 9a, 9b, and 9c may be utilized in any of the sensor embodiments discussed herein, as appropriate for the particular embodiment or portion thereof. Also, the end of the jumper that is not shown in the views of FIGS. 9a-9c, and that is opposite the terminus 924b, may have the same design (including the same type of attachment or coupling to the sensor substrate 914 and the conductive pattern 922 (including contact pad 923b)) as the one at terminus 924b, or it may have any of the other designs discussed herein.

Figure 10A:
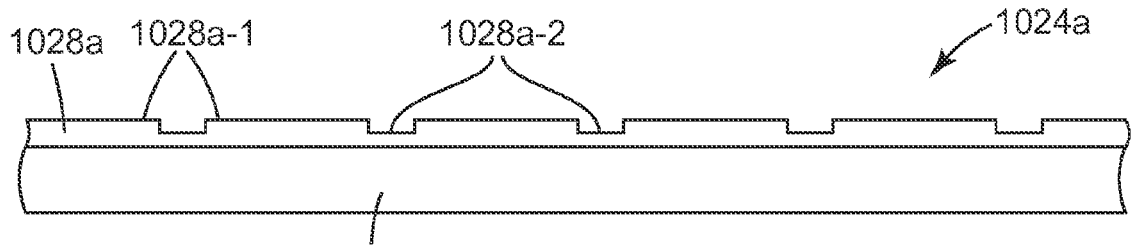
FIGS. 10a and 10b are schematic side or cross-sectional views of various jumpers for use in wetness sensors, the jumpers each having a conductive member of variable thickness.
Figure 10B:
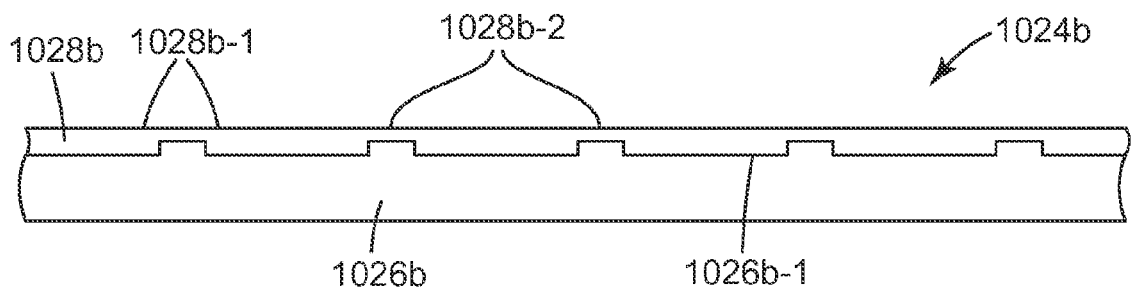

FIGS. 10a and 10b are schematic side or cross-sectional views of jumpers for use in wetness sensors, the jumpers each employing a conductive member of variable thickness. The combination of relatively thicker and relatively thinner portions of a given conductive member can be used to advantage in any of the disclosed embodiments. The thicker portions can, for example, help provide enhanced electrical properties by helping to provide sufficiently high electrical conductivity and sufficiently low electrical resistivity of the conductive member. The thinner portions can, for example, help provide regions of the conductive member that are more susceptible to breakage than the thicker regions when the jumper substrate begins to dissolve, swell, or otherwise degrade when contacted with the target fluid. Providing specific regions susceptible to breakage can help to provide more predictable or reliable failure mechanisms for the wetness sensors. Note that in exemplary embodiments, the conductive member as a whole, considered by itself, remains non-self-supporting as described elsewhere herein, although in some cases some or all of the thicker regions of the conductive trace, considered individually or separately, may be self-supporting. Furthermore, in exemplary embodiments, both the thinner and the thicker portions of the conductive member are thinner than a thickness of the jumper substrate, and both the thinner and the thicker portions of the conductive member are preferably thinner than 1 micron or 100 nanometers, for example. In some cases, the thicker sections are at least two times the thickness of the thinner sections. Other thickness relationships are also contemplated, keeping in mind the tradeoff between frangibility and electrical performance of the circuit.

Turning then to FIG. 10a, we see there a jumper 1024a for use in the disclosed wetness sensors, the jumper 1024a including a jumper substrate 1026 that may be self-supporting, and that may be adapted to dissolve, swell, or otherwise degrade when contacted with a target fluid. A conductive member 1028a has been formed on the substrate 1026, e.g., by printing, coating, etching, electrodeposition, vapor deposition, thermographic transfer, and/or other known patterning techniques. The conductor 1028a may be composed of a metal or other suitable electrically conductive materials, such as graphite and/or one or more conductive polymers, for example. The conductor 1028a is preferably so mechanically delicate that it is unable to maintain its physical integrity in the absence of the supporting substrate 1026. Conductive member 1028a, when considered by itself, may thus not be self-supporting, even though in some cases some or all of the thicker regions of the conductive member, considered individually or separately, may be self-supporting.

As shown, the conductor 1028a exhibits a variable thickness. Conductor 1028a thus includes both thicker portions 1028a-1 and thinner portions 1028a-2. The variable thickness can be provided using a variety of fabrication techniques. For example, if thin film evaporation is used to form the trace, baffles or shields can be employed to reduce the film thickness in selected areas. If printing is used to form the conductor, multiple passes can be employed, or printing parameters can be manipulated, to build up the film thickness in selected areas. If an etching process is used to form the conductor, selective etching can be used to reduce the film thickness in selected areas.

The jumper 1024b of FIG. 10b is also suitable for use in the disclosed wetness sensors, and the thickness profile of the conductive member is similar in some respects to that of jumper 1024a of FIG. 10a. The jumper 1024b includes a jumper substrate 1026b that is preferably self-supporting, and that may be adapted to dissolve, swell, or otherwise degrade when contacted with a target fluid. A conductive member 1028b has been formed on the substrate 1026b, e.g., by printing, coating, etching, electrodeposition, vapor deposition, thermographic transfer, and/or other known patterning techniques. The conductor 1028b may be composed of a metal or other suitable material, as discussed elsewhere herein. The conductor 1028b is applied sufficiently heavy or thick so that that the metal is thicker in the recessed areas of the profiled backing and thinner in the raised areas of the profiled backing, and does not just follow the contours of the profiled backing, especially when applied by electrodeposition or vapor deposition. Furthermore, the conductor 1028*b* is preferably not self-supporting as a whole, and particularly not the thinner portions thereof.

The conductor 1028*b* exhibits a variable thickness. The thickness variation pattern or profile is similar to that of conductive member 1028*a* (FIG. 10*a*), but the structured surface 1026*b*-1 corresponding to the thickness variation is an interior or "buried" interface between the conductive member 1028*b* and the substrate 1026*b*, rather than being an exterior or exposed surface of the conductive member 1028*b*. The result, however, is again that the conductive member 1028*b* exhibits a variable thickness, including both thicker portions 1028*b*-1 and thinner portions 1028*b*-2. The variable thickness can be provided using a variety of fabrication techniques. For example, before forming the conductive member 1028*b* on the substrate 1026*b*, the exposed surface of the substrate can be microstructured to form surface 1026*b*-1 e.g. by embossing or by using a continuous cast and cure (3C) process, for example. Conductive material that forms conductive member 1028*b* can then be deposited onto the structured surface 1026*b*-1 by printing or by other methods to produce a conductive member whose exposed surface is substantially flat, yet whose thickness changes along the length of the conductor.

Preferably, the thickness profiles provide thinned regions that are separated from each other by substantially longer lengths of thicker regions. Such designs advantageously maximize the conductivity (and minimize the resistivity) of the conductor, while still providing a plurality of spaced-apart thinned regions to promote RF circuit failure if the target fluid contacts the substrate. Buried interface designs such as that of FIG. 10*b* are advantageous from a manufacturing standpoint compared to exposed structured surface designs such as that of FIG. 10*a*.

Figure 10C:
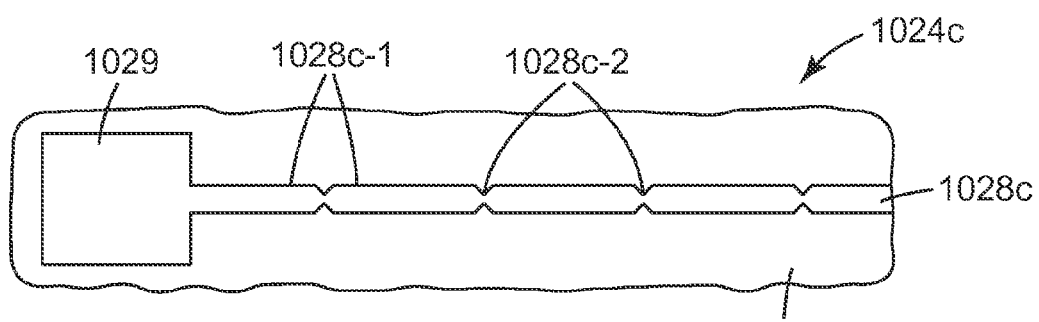
FIG. 10c is a schematic plan view of a jumper for use in wetness sensors, the jumper having a conductive member of variable width.

FIG. 10*c* is a schematic plan view of another jumper 1024*c* suitable for use in the disclosed wetness sensors. The jumper 1024*c* includes a jumper substrate 1026 and a conductive member 1028*c* applied to the substrate. Characteristics of jumper substrates and conductive member discussed elsewhere herein are equally applicable to those of FIG. 10*c*. Similar to the jumpers of FIGS. 10*a* and 10*b*, jumper 1024*c* provides distinct regions of the conductive member that makes the conductor more susceptible to breakage in such regions. In FIG. 10*c*, these regions are characterized by a reduction in the transverse in-plane dimension, or width, of the conductive member in a sequence of spaced-apart regions. Consequently, the conductor 1028*c* has a variable width. Relatively narrower portions 1028*c*-2 are distributed along the length of the conductor 1028*c*, separated by relatively wider portions 1028*c*-1 of the conductor. The wider portions enhance the electrical conductivity and reduce the electrical resistivity of the conductive member.

The reader will understand that the embodiments of FIGS. 10*a* through 10*c* are meant to be exemplary and not limiting. Design variations are contemplated. Thickness or width profiles other than V-shaped or rectangle-shaped features can be used. The relative spacing of the reduced thickness or reduced width regions can be selected as desired. In some cases, only one such reduced thickness or reduced width region may be used along the entire length of the conductive member or jumper. Furthermore, features of the different embodiments are intended to be mixed and matched. Embodiments may incorporate both one or more reduced thickness regions and one or more reduced width regions in a given conductive member. In some respects, variations in thickness of the conductive member are more advantageous than variations in width because, given the surface area constraints of a given system, increasing the thickness of the trace will result in a larger change in electrical impedance than increasing the width of the trace. Exemplary thicknesses used for the conductive trace are less than the skin depth of the electrical signal at the RF operating frequency, and increasing the thickness of the trace allows more area for the RF signal to travel.

EXAMPLES

Example 1

Figure 11A:
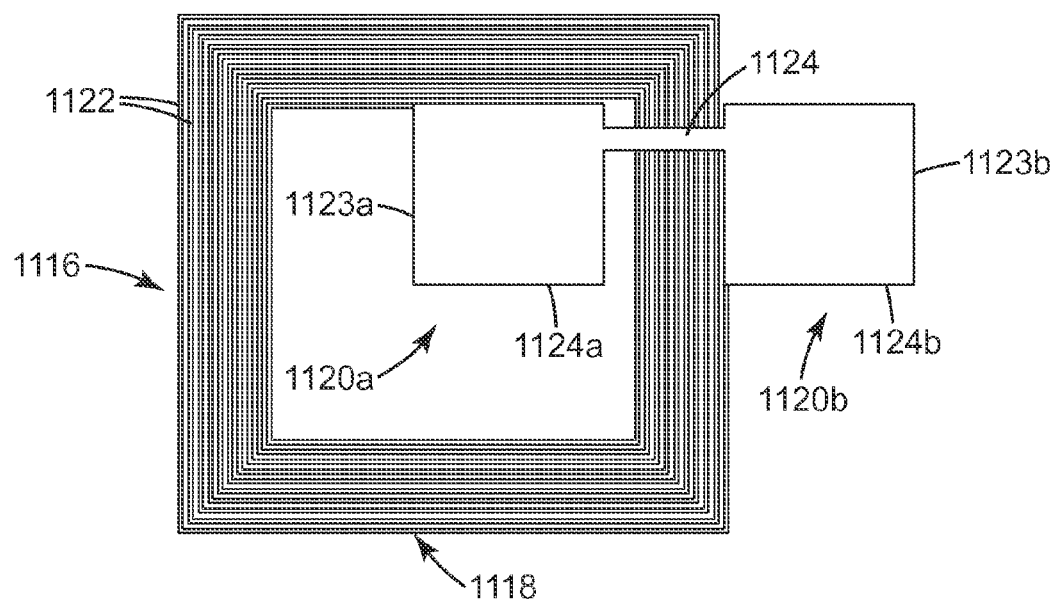
FIG. 11a is a schematic plan view of a tuned RF circuit for use in wetness sensors.

FIG. 11*a* depicts a tuned RF circuit 1116 suitable for use in the disclosed wetness sensors. The circuit includes a conductive pattern 1122 that has been printed on a flexible sensor substrate (not labeled), the pattern 1122 including a pad 1123*a* at an inner terminus of the pattern and a pad 1123*b* at an outer terminus of the pattern, the pattern also being shaped to provide an inductive coil 1118. For purposes of this example, the pads 1123*a*, 1123*b* were each assumed to be square-shaped, with the length of one side of the squares being 14.5 mm, corresponding to an area of 0.000210 $m^2$. A dumbbell-shaped jumper 1124, with square ends coinciding in size and shape to the pads of the conductive pattern, capacitively couples to pad 1123*a* at a first square-shaped terminus 1124*a* of the jumper, forming a first capacitor 1120*a*. The jumper also capacitively couples to pad 1123*b* at a second square-shaped terminus 1124*b* of the jumper opposite the first terminus, thus forming a second capacitor 1120*b*. Each capacitor was also assumed to include a square-shaped piece of insulating material, the insulating material being coextensive with the respective pad of pattern 1122 and terminus of jumper 1124, the insulating material assumed to have a thickness of 50 microns and a dielectric constant K (see discussion below) of 3.5. The first and second capacitors are connected to the inductive coil in the manner shown in FIG. 2*b*. In the plan view of FIG. 11*a*, the square-shaped terminuses of the jumper 1124 obstruct the view of the square-shaped insulating pieces and the square-shaped pads of pattern 1122.

The circuit 1116 was computationally modeled to determine if it was feasible to construct a practical embodiment having a resonant frequency of 13.56 MHz, which is a frequency band reserved in the United States for industrial, scientific, and medical (ISM) devices, and is widely used in the U.S. for RFID devices. We assumed the coil 1118 was a generally square-shaped inductive coil used in RFID devices, e.g., made of copper having a trace thickness of about 35 microns (corresponding to so-called "1 ounce copper"), with about 8 turns or loops to the coil, the outer border or envelope of which is a square whose side length is 40 millimeters (about 1.5 inches). A coil of these design parameters has an inductance of about 3.4 micro-Henries.

Figure 11B:
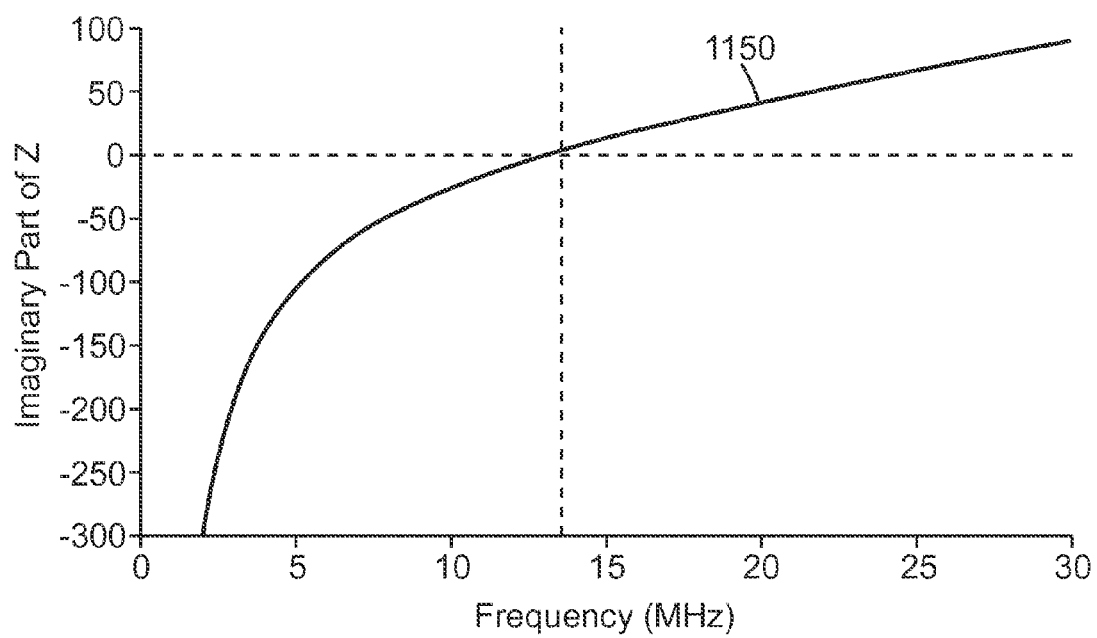

This circuit was modeled using a computer program that calculates the complex impedance Z of the circuit. The imaginary part of the calculated impedance Z is plotted as a function of frequency in FIG. 11*b*, see curve 1150. The frequency at which the imaginary part of Z is zero corresponds to the resonant frequency of the circuit. Curve 1150 has a zero value at a frequency that is slightly less than 13.56 MHz. These modeling results indicate that a tuned RF circuit of reasonable design parameters can be made to have a resonance frequency equal to the standard 13.56 MHz frequency, if slight modifications to the modeled parameters are made, such as any of the dimensions associated with the capacitors 1120*a*, 1120*b*.

Figure 12:
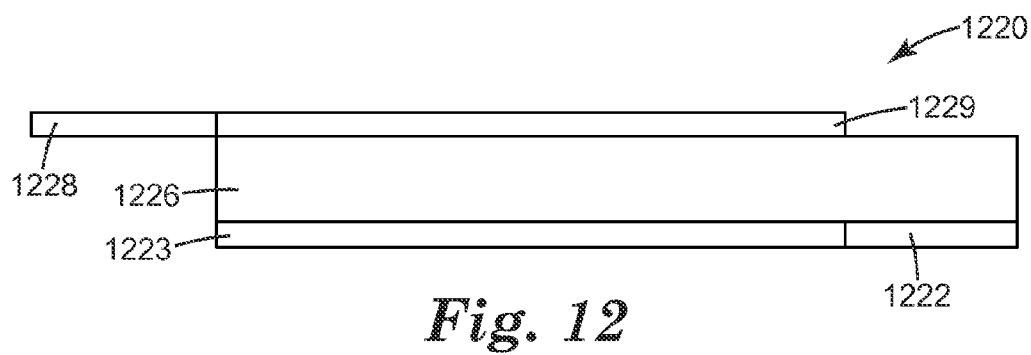
FIG. 12 is a schematic side or sectional view of a capacitor formed between a terminus of a jumper and a terminus of a conductive pattern, the capacitor including a frangible link, representative embodiments of which were fabricated and tested.

Also constructed and tested were individual capacitors made with a dissolvable film, such capacitors thus being suitable for use as frangible links in the disclosed wetness sensors. For these experiments, a 2-mil (about 51 micrometer) thick sheet of polyvinyl alcohol (PVA) thermoplastic material (MonoSol™ M8630 film, available from MonoSol, LLC, Portage, Ind., USA) was used as the dissolvable film. Silver was vapor coated to one side of this film to a thickness of about 90 nanometers. A strip of this film was joined to a strip of copper tape of the same width. The copper tape was 3M™ 119194 Tape (Copper Foil with Conductive Adhesive), which has a 40 micron thick layer of copper and a thinner (approx. 26 micron thick) layer of electrically conductive pressure sensitive adhesive. The adhesive-side of the copper tape was applied to a strip of the silver-coated PVA to produce a capacitor similar to that shown in FIG. 12. FIG. 12 depicts in simplified fashion an exemplary capacitor 1220, where 1226 refers to a dissolvable film (e.g. the piece of PVA film), 1228 refers to a conductive member (e.g. the copper layer with conductive adhesive) having a tab 1229, and 1222 refers to a conductive pattern 1222 having a contact pad 1223 (e.g. the silver coating on the PVA). Note, in the constructed examples, the width of the copper tape was substantially uniform, such that no distinct tab 1229 was formed in the conductive member 1228, and the width of the silver conductor was also substantially uniform, such that no distinct pad 1223 was formed in the pattern 1222.

Several sample capacitors were made, some utilizing copper and PVA strips that were 1 inch wide (and that overlapped in a 1 by 1 inch square, corresponding to a capacitor area of about 0.000645 square meters), others utilizing copper and PVA strips that were 0.5 inches wide (and that overlapped in a 0.5 by 0.5 inch square, corresponding to a capacitor area of about 0.000161 square meters). The capacitance of the constructed capacitors was measured in the vicinity of 13.56 MHz using an Agilent™ Precision Impedance Analyzer, model 4294A, using a model 42941A probe, and the dielectric constant K of the PVA was calculated using the following relationships:

$$C = \frac{\varepsilon A}{d},$$

and $$K = \frac{\varepsilon}{\varepsilon_0},$$

where C is the measured capacitance, $\varepsilon$ is the permittivity of the PVA insulator, A is the cross-sectional area of the square piece of PVA insulator (and the area of each capacitor "plate"), d is the separation between capacitor plates (in this case, the 51 micron thickness of the PVA insulator film), K is the dielectric constant of the PVA insulator, and $\varepsilon_0$ is the permittivity of free space ($8.854 \times 10^{-12}$ $C^2/N \cdot m^2$). The results were as follows:

TABLE 1

| Sample | A | Measured Capacitance (pF) | K |
|---|---|---|---|
| 1 | 0.000645 m² | 11.5 | 0.101 |
| 2 | 0.000645 m² | 400 | 3.50 |
| 3 | 0.000645 m² | 370 | 3.24 |
| 4 | 0.000645 m² | 320 | 2.80 |
| 5 | 0.000645 m² | (shorted) | — |
| 6 | 0.000161 m² | 100 | 3.51 |
| 7 | 0.000161 m² | 104 | 3.64 |

Sample 5 yielded no capacitance measurement because the silver conductor and the copper tape were short-circuited.

Reviewing the results, we see that the 1 by 1 inch (0.000645 m²) capacitors exhibited fairly consistent results in the range from 300 to 400 picoFarads. The errant or outlying result for sample 1 at 11.5 pF was caused by using a piece of silver-coated PVA that had a much thinner coating of silver compared to the other samples (i.e., much thinner than 90 nm), due to being near the end of the silver-coated roll from which the piece was cut. The smaller half-inch by half-inch (0.000161 m²) capacitors exhibited relatively consistent results of about 100 pF. These results are in keeping with the equation above that shows the capacitance C is directly proportional to the area A. The area ratio of the bigger 1-inch capacitors to the smaller half-inch capacitors is 4-to-1, and the ratio of the measured capacitances for these capacitor types is also about 4-to-1, as one would expect from the equation. The results above indicate that the dielectric constant for the PVA material used in the examples is about 3.5.

Although these capacitors were not exposed to a target fluid, that from these results we can expect tuned RF circuits incorporating such capacitors to exhibit a change in impedance of at least a factor of 5, 10, 100, or 1000, or to exhibit an open circuit, or that the RF circuit would be rendered inoperative, if exposed to water or other target fluid.

Examples 2-10

Examples 2 through 10 describe the fabrication of strip-shaped and U-shaped samples having a layer of conductive material completely covering one major surface or side of the respective strip-shaped or U-shaped substrate. Such samples may be used, for example, as jumpers having frangible links in the disclosed tuned RF circuits.

Example 2

Individual sheets of polyvinyl alcohol (PVA) film (available as "Monosol M8630" from Monosol, LLC, Portage, Ind., USA) having measured thicknesses of 2, 4, and 6 mils (about 51, 102, and 153 micrometers respectively) were used as self-supporting substrates. Silver films were coated onto 127 mm by 178 mm samples of the PVA film substrates by magnetron physical vapor deposition. The silver films were sputter deposited from a silver metal target. The PVA substrates were placed on a substrate holder set up inside a vacuum chamber with a sputtering silver target located at a height of 178 mm above the substrate holder. After the chamber was evacuated to $1 \times 10^{-5}$ torr base pressure, sputter gas argon was admitted inside the chamber at a flow rate of 50 sccm (standard cubic centimeter per minute) using a mass flow controller. The total pressure of the chamber was adjusted to 2 milliTorr. Sputtering was initiated using a DC power supply at a constant power level of 0.10 kilowatts. The sputter duration was varied to produce samples having different silver film thickness. For example, coating using a power level of 0.10 kilowatts for 7 minutes produced a sample with a silver film thickness of 140 nm. The substrate was not heated and was kept at room temperature. The thickness of the silver film deposited on the samples was determined by measuring the thickness of silver deposited on silicon wafers that were placed next to the samples during the coating process. The thickness of silver deposited on the wafers was determined using a KLA Tencor Model P-15 Profilometer (available from KLA Tencor Corporation, San Jose, Calif., USA).

Individual strip-shaped samples (having dimensions of 25 mm by 152 mm) were cut from the silver coated PVA substrate sheet. The individual samples were tested for disintegration and dissolution of the substrate using the following method. A 500 milliliter beaker filled with saline solution (0.9% NaCl) was maintained at ambient temperature (20.5° C.) and agitated with stirring. The individual samples of the silver coated substrate were immersed in the saline solution so that the entire sample was covered by liquid. The time required for sample disintegration and sample dissolution was measured in seconds. Sample disintegration was defined as the point where the substrate film began to break apart, creating breaks in the silver coating. Dissolution was defined as the point where the substrate film totally dissolved in the liquid, leaving small particles of silver suspended in the liquid. The results are reported in Table 2.

TABLE 2

| Thickness of Silver Coating (nm) | Thickness of PVA Substrate (mil) | Disintegration Time (seconds) | Dissolution time (seconds) |
| --- | --- | --- | --- |
| 40 | 2 | 12 | 25 |
| 90 | 2 | 13 | 29 |
| 140 | 2 | 15 | 40 |
| 140 | 4 | 780 | not determined |
| 140 | 6 | >1080 | not determined |

Example 3

A sheet of PVA film (available as "Monosol M8630" from Monosol, LLC, Portage, Ind., USA) having a measured thickness of 2 mils (about 51 micrometers) was sputter deposited with silver by magnetron physical vapor deposition at a thickness of 40 nm according to the procedure described in Example 2. A sample strip (25 mm by 152 mm) was cut from the silver coated PVA substrate sheet and placed on a non-conductive surface. The sample was tested for resistance before and after wetting with a saline solution. Using a Simpson Model 260 Ohmmeter (Simpson Electric, Lac du Flambeau, Wis., USA), the test leads of the ohmmeter were attached to opposite ends of the sample. The meter was set to record measurements over a range of 0 to 2000 ohms. An initial resistance reading of about 0 ohms was measured. After pouring a single portion of saline solution (0.5 mL of 0.9% NaCl) onto the center region of the sample, the silver coated PVA film disintegrated, creating breaks in the silver coating. The resistance measurement changed from 0 ohms to 2000 ohms (the maximum instrument setting) over a period of 10 seconds.

Example 4

The same procedure as described in Example 3 was followed, except that the saline solution was replaced with 1.0 mL of a simulated wound fluid solution. The simulated wound fluid solution was prepared by dissolving sodium chloride (2.07 g) and calcium chloride (0.07 g) in deionized water (247.9 g) according to the procedure described in U.S. Patent Application Publication US 2011/0040289 (Canada et al.). The sample was tested for resistance before and after exposure to the simulated wound fluid. Using a Smart Electrician Model 364-5017 Digital Meter (available from Menards Corporation, Eau Claire, Wis., USA), the test leads of the ohmmeter were attached to opposite ends of the sample. The meter was set to record measurements over a range of 0 to 300 ohms. An initial resistance reading of 0 ohms was measured. After pouring a single portion of simulated wound fluid solution (1.0 mL) onto the center of the sample, the silver coated PVA film disintegrated, creating breaks in the silver coating. The resistance measurement changed from 0 ohms to 300 ohms (the maximum instrument setting) over a period of 11 seconds.

Example 5

A square sheet (76 mm by 76 mm) of expanded polystyrene foam (EPF) having an initial measured thickness of 1.8 mm was compressed at 170° C. and 34,500 kPa (5000 psi) for 18 seconds using a Model 3912 Carver Hydraulic Press (Carver Corporation, Wabash, Ind., USA) to provide a 0.23 mm thick sample. The compressed sheet of EPF was used as a self-supporting substrate. The entire surface of the EPF sheet was then flood coated with CI-1001 conductive ink (available from ECM Corporation, Delaware, Ohio, USA) using a Mayer rod (number 3). The coating thickness was about 1.7 grams per square meter (gsm). The printed sheet was placed in an oven at 50° C. for 30 minutes. After cooling to ambient temperature, a 76 mm by 13 mm strip was cut from the printed EPF sheet. The strip-shaped sample was tested for resistance before and after exposure to unleaded gasoline. Using the Smart Electrician Model 364-5017 Digital Meter, the test leads of the ohmmeter were attached to opposite ends of the sample. The meter was set to record measurements over a range of 0 to 300 ohms. An initial resistance reading of 0 ohms was measured. The sample with leads attached was placed in a glass petri dish, and unleaded gasoline (10 mL) was added to the petri dish to create a pool of gasoline about 6 mm in depth. On initial set-up, the sample with leads attached was carefully flexed so that the leads would not be in contact with the gasoline solvent. The coated EPF strip disintegrated after contact with the gasoline, creating breaks in the conductive ink coating. Over a period of 44 seconds starting from the addition of the gasoline to the sample, the resistance measurement changed from 0 ohms to 300 ohms (the maximum instrument setting).

Example 6

An adult sized mannequin designed for the testing of absorbent articles (available from Marketing Technology Service, Inc., Kalamazoo, Mich., USA) was obtained. The mannequin was arranged in a standing position. A Masterflex Peristalic L/S Pump (available from Cole-Parmer, Vernon Hills, Ill., USA) was used to pump saline solution (0.9% NaCl) through the male or female outlet of the mannequin. The mannequin was fitted with a Medline Comfort-Aire Unisex Disposable Brief diaper having a hip size of 40-50 inches (available from Medline Industries, Mundelein, Ill., USA). The sensor part of the assembly was prepared from a sheet of 305 mm by 254 mm PVA film (2-mil thickness) sputter coated on one side with silver (40 nm thickness) according to the procedure described in Example 2. The film was then cut using a laser to provide a generally U-shaped sample, the shape shown in plan view in FIG. 12a. In reference to that figure, the length L1 of the two parallel sides was about 190 mm, the length L2 of the other side was about 15 mm, and the width w was about 5 mm. A laminate was prepared by attaching the sample (silver side up) to tissue paper (220 mm by 40 mm sheet) using a minimum amount of a spray adhesive (available as "3M™ Super 77™ Multipurpose Adhesive" from 3M Company, Maplewood, Minn., USA). The sample was positioned in the center of the tissue paper so that about 25 mm of the open ends of the two parallel sides extended beyond the edge of the tissue paper. The laminate was attached with the same spray adhesive to the backsheet on the inside front portion of the diaper at a position 90 mm from the top of the waist band. The sample side of the laminate was directed toward the mannequin. A small hole was cut through the back sheet of the diaper so that the two ends of the U-shaped sample that extended beyond the tissue paper backing could be inserted through the hole and attached using alligator clips to an Agilent 4294A Precision Impedance Analyzer (available from Agilent Technologies, Santa Clara, Calif., USA). The operation of the pump and recording of impedance data was automated using LabView software (available from National Instruments, Austin, Tex., USA).

Saline solution was added to the diaper through the inlet port in the mannequin at the set rate of 4 mL/sec. At an elapsed time of about 40 seconds, a shift in the impedance measurement from 0 ohms to about 200 ohms was detected. At an elapsed time of 155 seconds, a further shift in impedance to greater than 1000 ohms was detected. Measurements of impedance versus time are presented in Table 3. Visual examination of the laminate at the end of the experiment showed that the PVA substrate had dissolved, destroying the integrity of the sensor. Similar results were obtained using either the male or female outlet port.

TABLE 3

| Elapsed Time (seconds) | Real Impedance (ohms) | Imaginary Impedance (ohms) | Total Liquid (ml) |
| --- | --- | --- | --- |
| 0.5 | 0 | 0 | 2 |
| 5 | 22.0 | −14.7 | 20 |
| 15 | 21.6 | −14.1 | 60 |
| 25 | 21.2 | −13.9 | 100 |
| 35 | 24.2 | −14.4 | 140 |
| 45 | 217.2 | −60.6 | 180 |
| 55 | 318.3 | −86.7 | 220 |
| 65 | 309.4 | −79.4 | 260 |
| 75 | 359.2 | −100.4 | 300 |
| 85 | 362.1 | −102.0 | 340 |
| 95 | 411.0 | −125.1 | 380 |
| 105 | 411.4 | −125.5 | 420 |
| 115 | 422.0 | −128.0 | 460 |
| 125 | 431.9 | −131.0 | 500 |
| 135 | 671.4 | −332.3 | 540 |
| 145 | 794.1 | −435.2 | 580 |
| 155 | 1012.8 | −621.7 | 620 |
| 165 | 1066.2 | −650.3 | 658 |

Example 7

Samples with conductive traces having non-uniform thickness were prepared from sheets of PVA film (2-mil thickness) sputter coated on one side with silver according to the procedure described in Example 2, except that, in order to obtain a non-uniform thickness of the conductive material, a pattern template was placed over the film to mask or prevent specified regions of the PVA substrate from being coated. With the pattern template in place, the PVA film was sputter coated to provide a first coating of silver (40 nm thickness). The template was then removed, and a second coating of silver (40 nm thickness) was applied. The result was a pattern in which some regions of the film were coated with silver of 80 nm thickness, and the remaining regions of the film were coated with silver of only 40 nm thickness.

Figure 12A:
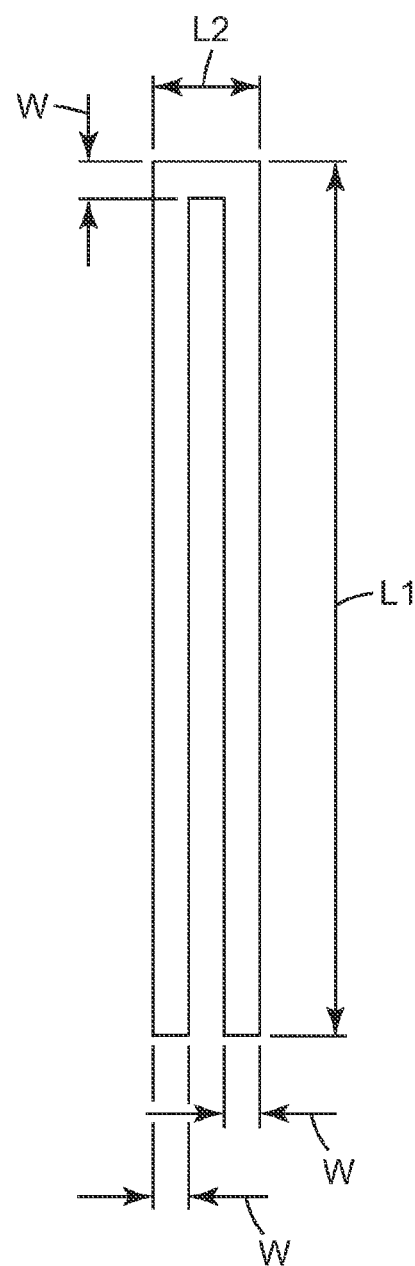
FIG. 12a is a U-shaped component suitable for use in the disclosed wetness sensors.

The coated film was cut using a laser to prepare U-shaped samples as shown generally in FIG. 12*a*, where the length L1 of the two parallel sides was about 99 mm, the length L2 of the other side was about 15 mm, and the width w was about 5 mm.

Five samples (referred to herein as Samples 7a through 7e) containing different patterns of variable thickness in the conductive silver layer were prepared. Two samples (referred to herein as Samples 7f and 7g) were prepared having a conductive silver layer of uniform thickness.

In Sample 7a, the conductive layer contained four regions of 80 nm thick coated silver, with each region having an area of 8 mm by 5 mm. The four regions were equally positioned on the two parallel sides of the U-shaped substrate (2 regions on each side) starting at positions 5 mm from the upper (closed) end of the shape (as seen from the perspective of FIG. 12*a*) and at the lower (open) end of the shape. For Sample 7a, 16% of the total area of the conductive layer had a silver coating of 80 nm thickness, and the remaining area had a silver coating of 40 nm thickness.

In Sample 7b, the conductive layer contained eight regions of 80 nm thick coated silver with each region having an area defined by a square of 5 mm by 5 mm. The eight regions were equally positioned on the two parallel sides of the U-shaped substrate (4 regions on each side) starting at positions 10 mm from the upper (closed) end of the shape (refer to FIG. 12*a*) and 5 mm from the lower (open) end of the shape. For Sample 7b, 20% of the total area of the conductive layer had a silver coating of 80 nm thickness, and the remaining area had a silver coating of 40 nm thickness.

In Sample 7c, the conductive layer contained ten regions of 80 nm thick coated silver with each region having an area defined by a square of 5 mm by 5 mm. The ten regions were equally positioned on the two parallel sides of the U-shaped substrate (5 regions on each side) starting at positions 8 mm from the upper (closed) end of the shape (refer to FIG. 12*a*) and 2 mm from the lower (open) end of the shape. For Sample 7c, 25% of the total area of the conductive layer had a silver coating of 80 nm thickness and the remaining area had a silver coating of 40 nm thickness.

In Sensor Sample 7d, the conductive layer contained sixteen regions of 80 nm thick coated silver with each region having an area defined by a square of 5 mm by 5 mm. The sixteen regions were equally positioned on the two parallel sides of the U-shaped substrate (8 regions on each side) starting at positions 8 mm from the upper (closed) end of the shape (refer to FIG. 12*a*) and 5 mm from the lower (open) end of the shape. For Sample 7d, 40% of the total area of the conductive layer had a silver coating of 80 nm thickness and the remaining area had a silver coating of 40 nm thickness.

In Sensor Sample 7e, the conductive layer contained eight regions of 40 nm thick coated silver with each region having an area defined by a square of 5 mm by 5 mm. The eight regions were equally positioned on the two parallel sides of the U-shaped substrate (4 regions on each side) starting at positions 10 mm from the upper (closed) end of the shape (refer to FIG. 12*a*) and 5 mm from the lower (open) end of the shape. For Sample 7e, 20% of the total area of the conductive layer had a silver coating of 40 nm thickness and the remaining area had a silver coating of 80 nm thickness.

Sample 7f was prepared with a uniform silver coating of 40 nm thickness, and Sample 7g was prepared with a uniform silver coating of 80 nm thickness.

Impedance measurements for Samples 7a through 7f were determined using an Agilent 4294A Precision Impedance Analyzer with a 42941A Impedance Probe (available from Agilent Technologies, Santa Clara, Calif., USA). The instrument was swept from 8 MHz to 15 MHz and the probe was calibrated using open and short calibration standards. On the impedance analyzer a mark was placed at 13.56 MHz to display the values of the real and imaginary parts of the impedance. The sample and probe were placed on a non-conductive surface, and impedance was measured across the open end of the sample (i.e., the lower ends of the shape shown in FIG. 12a) by attaching the probe about 1 mm from the ends of the U-shaped sample. The results are reported in Table 4 as the average of six measurements.

Sample 7e was placed on a dry paper towel (trade designation "WypAll", available from Kimberly-Clark Corporation, Neenah, Wis.) and the open ends of the conductive sample were attached to the leads of the impedance probe. Tap water (1.0 mL) was placed directly on a portion of Sample 7e that contained regions of both thick silver coating (80 nm) and thin silver coating (40 nm). Disintegration of the thin coated region was observed at 13 seconds after the addition of water, while the thick coated region began to disintegrate at 30 seconds after the addition of water. The initial real impedance measurement of 18 ohms began to shift beginning at 9 seconds after the addition of water. At the 13 second time point, where disintegration of the thin coated region was observed, the real impedance measurement was greater than 1000 ohms.

TABLE 4

| Sensor Sample | Real Impedance (ohms) | Imaginary Impedance (ohms) |
| --- | --- | --- |
| 7a | 43 | 4.8 |
| 7b | 52.5 | 4 |
| 7c | 55.5 | 3.5 |
| 7d | 42 | 4.7 |
| 7e | 18 | 5 |
| 7f | 65 | 4 |
| 7g | 17 | 5 |

Example 8

Sample 7f described in Example 7 was attached with adhesive tape (under the trade designation Scotch® Transparent Tape, available from 3M Company, Maplewood, Minn., USA) to a 102 mm by 102 mm piece of dry wall (available from Lafarge North America, Washington, D.C.). The impedance measurements were determined using an Agilent 4294A Precision Impedance Analyzer with a 42941A Impedance Probe (available from Agilent Technologies, Santa Clara, Calif., USA). The instrument was swept from 8 MHz to 15 MHz and the probe was calibrated using open and short calibration standards. On the impedance analyzer a mark was placed at 13.56 MHz to display the values of the real and imaginary parts of the impedance. The leads of the probe were attached to the open end of the trace and the initial impedance value was measured for a dry sample. An initial impedance of the dry sample was measured. The sample attached to dry wall was submerged into a tray containing tap water so that about 25.4 mm (1 inch) of the sample (starting from the end opposite from the attachment of the leads) was under water. An impedance shift was recorded within 5 seconds of submersion of the sample into the water. At 30 seconds, the silver coated PVA film disintegrated, creating breaks in the silver coating. The impedance measurements for the dry sample and the sample after submersion in tap water for 30 seconds are presented in Table 5.

TABLE 5

| Sample | Initial Real Impedance (dry sample) (ohms) | Initial Imaginary Impedance (dry sample) (ohms) | Final Real Impedance (wet sample) (ohms) | Final Imaginary Impedance (wet sample) (ohms) |
| --- | --- | --- | --- | --- |
| Sample 7f attached to drywall | 15 | 6 | 1000 | −1400 |

Example 9

A sheet of polyvinyl alcohol (PVA) film (available as Monosol M8630 from Monosol, LLC, Portage, Ind., USA) having a measured thickness of 2 mils (about 51 micrometers) was sputter deposited with silver by magnetron physical vapor deposition according to the procedure described in Example 2. Three individual samples were prepared having silver coated at thicknesses of 141 nm, 187 nm, and 280 nm. Each sample of coated film was cut using a laser to provide a generally U-shaped sample, the shape shown in FIG. 12a. In reference to that figure, the length L1 of the two parallel sides was about 190 mm, the length L2 of the other side was about 15 mm, and the width w was about 5 mm. Impedance measurements were determined using an Agilent 4294A Precision Impedance Analyzer with a 42941A Impedance Probe (available from Agilent Technologies, Santa Clara, Calif., USA). The instrument was swept from 8 MHz to 15 MHz and the probe was calibrated using open and short calibration standards. On the impedance analyzer a mark was placed at 13.56 MHz to display the values of the real and imaginary parts of the impedance. The sample and probe were placed on a non-conductive surface and impedance was measured across the open end of the sample (i.e., the lower ends of the shape shown in FIG. 12a) by attaching the probe about 1 mm from the ends of the U-shaped sample. An initial impedance of the dry sample was measured. After adding 3.0 mL of artificial urine (available from Ward's Natural Science, Rochester, N.Y., USA) dropwise to the sample, an impedance shift was recorded within seconds of adding the liquid. Initial and final impedance measurements are reported for the three samples in Table 6.

TABLE 6

| Silver thickness (nm) | Initial Real Impedance (dry sample) (ohms) | Initial Imaginary Impedance (dry sample) (ohms) | Final Real Impedance (wet sample) (ohms) | Final Imaginary Impedance (wet sample) (ohms) |
| --- | --- | --- | --- | --- |
| 280 | 8.2 | 84.0 | 5740 | −75.0 |
| 187 | 7.9 | 87.0 | 4300 | −72.6 |
| 141 | 7.2 | 78.0 | 3000 | −79.6 |

Example 10

Prophetic

A sheet of polyvinyl alcohol (PVA) having a thickness of 2 mils (about 51 micrometers) can be fabricated to have thinner and thicker regions as depicted in FIG. 10b and can be used as the self-supporting substrate 1026b. Fabrication (for example by embossing) can form the depressed microstructured surface 1026b-1 at a depth of 40 nm, for example. The substrate can be flood coated with conductive ink to provide 40 nm ('thin') regions of conductive material (1028b-2) and 80 nm ('thick') regions of conductive material (1028b-1). The resulting exposed surface of the conductive ink coating may be substantially flat. The coated film can be cut using a laser to provide a generally U-shaped sample, substantially as shown in FIG. 12a. In reference to that figure, the length L1 of the two parallel sides may be 190 mm, the length L2 of the other side may be 15 mm, and the width w may be 5 mm. Any pattern of thick and thin regions may be used as long as at least one thin region (1028b-2) is present in the sensor. Impedance measurements can be made with any suitable impedance analyzer or ohmmeter. The sample and probe can be placed on a non-conductive surface, and the impedance may be continuously measured across the open end of the conductive sample by attaching the probe at the ends of the U-shaped sample. Water, saline solution, artificial urine, or simulated wound fluid can be added to the sample. The sample can be measured for impedance before and after wetting. The substrate may be observed to disintegrate (creating breaks in the trace) and a shift in the impedance by a factor of 100 to 1000 can be measured.

Example 11

A complete RF tag of the design described in connection with FIG. 4 was prepared. The conductive pattern was prepared by a copper etching process using a sheet of polyester film (thickness of 2 mils, i.e., about 51 micrometers) as the flexible substrate. The conductive pattern included a square-shaped spiral coil with six turns or loops. The width of the coil element was about 0.5 mm and the thickness was about 35 microns. The overall outer dimension of the square-shaped coil was about 40 mm (1.5 inches). The conductive pattern also included four small contact pads that were used for attachment of capacitor and jumper elements.

A discrete low ESR (Equivalent Series Resistance) thin film capacitor (series ACCU-P available from the AVX Corporation, Fountain Inn, S.C., USA) was used to tune the circuit to a frequency of 13.56 MHz with a Q-factor greater than 10. The capacitor was soldered onto two of the contact pads of the conductive pattern using a low-temperature melt solder.

The jumper element (comprising a frangible link) was prepared from a sheet of PVA film (thickness of 2 mils, i.e., about 51 micrometers) sputter coated on one side with silver according to the procedure described in Example 2. The film was cut with a laser to prepare a J-shaped jumper, as shown in FIG. 4, with the two parallel sides having lengths of about 127 mm and 67 mm, the other side having a length of about 5 mm, and the width of all sides being about 5 mm.

Strips (measuring 6.35 mm by 10 mm) of Z-axis Electrically Conductive Double Sided Tape (available from the 3M Company, St. Paul, Minn., USA) were attached to two of the contact pads of the trace and the finished jumper element was then attached to the conductive tape so that the silver side of the jumper was in contact with the conductive tape. This completed the circuit of the RF tag.

The RF tag was placed between the backsheet and absorbent core of a size 4 baby diaper (available under the trade designation "PAMPERS" from the Procter & Gamble Company, Cincinnati, Ohio, USA) with the patterned copper conductor positioned to face the absorbent core. A hand-held reader was used to measure the response of the RF tag. The reader contained an antenna that resonated at a frequency of 13.56 MHz to maximize communication with the RF tag. The gain/phase subcomponent of the "S11 parameter" of the reader antenna (known to those skilled in the antenna arts) was measured at start-up using a gain/phase detector (model AD8302 available from Analog Devices, Norwood, Mass., USA) to provide a baseline value. In an identical manner, the S11 parameter of a dry diaper with inserted RF tag was measured. If on interrogation of the diaper, the reader measured a change in the S11 parameter of at least 50% as compared to the calibration value, then the RF tag was determined to be dry—indicating an intact tag and dry diaper. If the reader measured a change in the S11 parameter less than 50% as compared to the calibration value, then the RF tag was determined to be wet—indicating a deterioration in the integrity of the jumper element and a wet diaper. Depending on the measurement reading, a green light was activated on the reader for a dry diaper and a red light was activated for a wet diaper.

Figure 13:
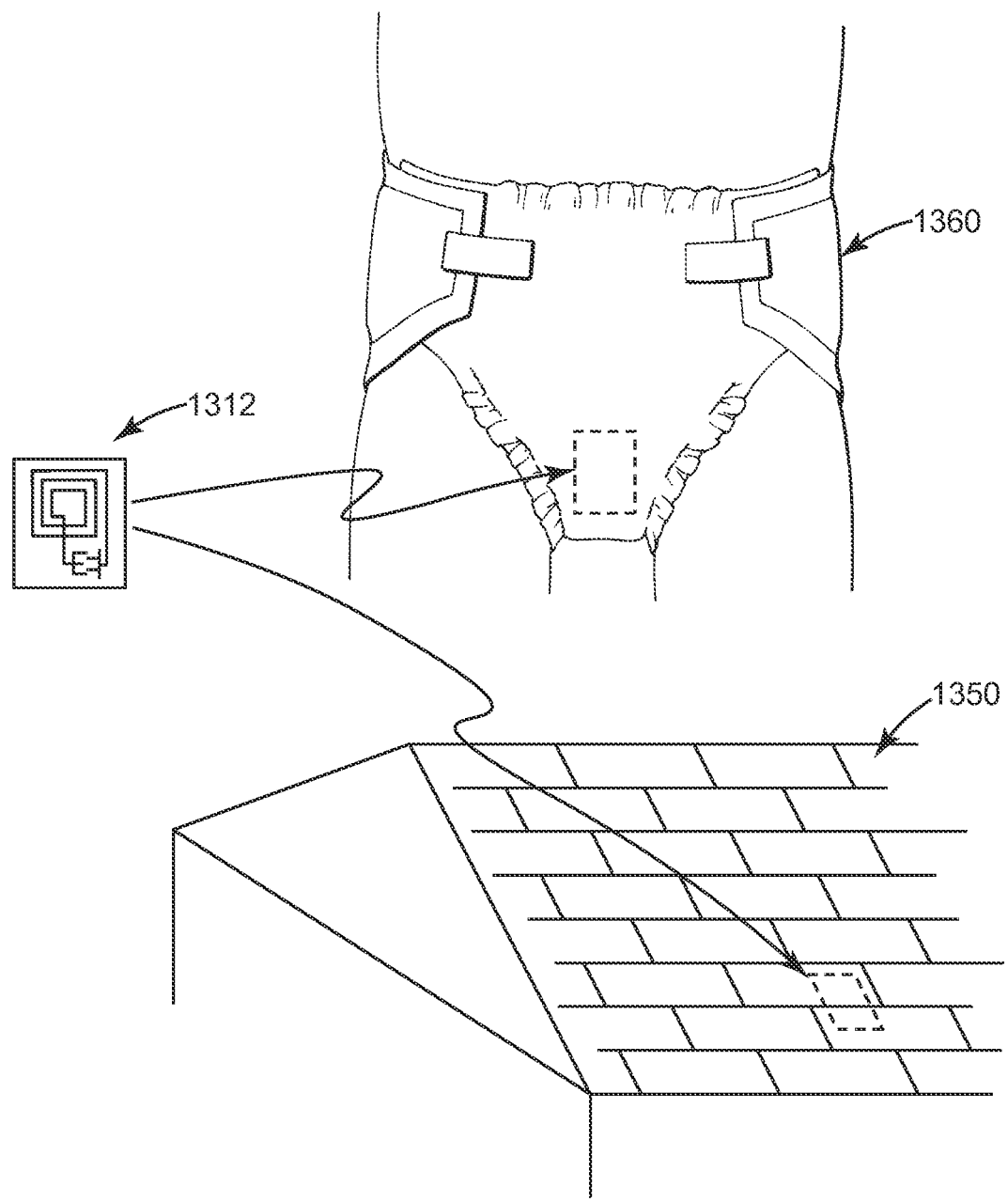
FIG. 13 is a schematic diagram showing different end-use applications of the wetness sensor.

In a test of the system, a freshly constructed diaper containing an RF tag as described in this Example 11 was scanned with the reader and the green light on the reader was activated indicating a dry diaper. A 100 mL portion of saline solution (0.9% NaCl) was then poured onto the top sheet of a diaper (in an area of the diaper where an insult of urine would normally occur). The diaper was re-scanned with the reader and within 30 seconds after the addition of saline solution, the red light on the reader was activated indicating a wet diaper. As such, the saline solution produced a drastic change in the RF tag and rendered it inoperative Further Embodiments and Applications FIG. 13 is a schematic diagram showing different end-use applications of the disclosed wetness sensors 1312. The depicted applications are merely exemplary, and are not intended to be limiting. On one application, the wetness sensor 1312 is inserted or otherwise incorporated into an absorbent garment such as a diaper 1360. In another application, the sensor 1312 is inserted or otherwise incorporated into a roof 1350, building, or similar structure. The sensor 1312 may for example be positioned underneath shingles, tiles, or other roofing materials in a place that would normally be expected to remain dry, but where the presence of moisture would be important to be aware of. In either case, wetness of the garment, building, or other article may be conveniently detected by remote monitoring of the sensor 1312 as discussed above.

The wetness sensor 1312 can be beneficially used in other applications, discussed above, in which it is desirable to detect wetness but difficult to visually or otherwise directly observe the wetness. The sensor 1312 may for example be incorporated into or otherwise attached to construction-related articles such as wall board, insulation, flooring, and roofing, as well as fittings and support structures to detect leakage from pipes underground, beneath floors, behind walls, or above ceilings, for example. Other applications may include incorporating the wetness sensor 1312 into packages or boxes to detect leakage or thawing, e.g. for medical or automotive applications, for example.

Figure 14A:
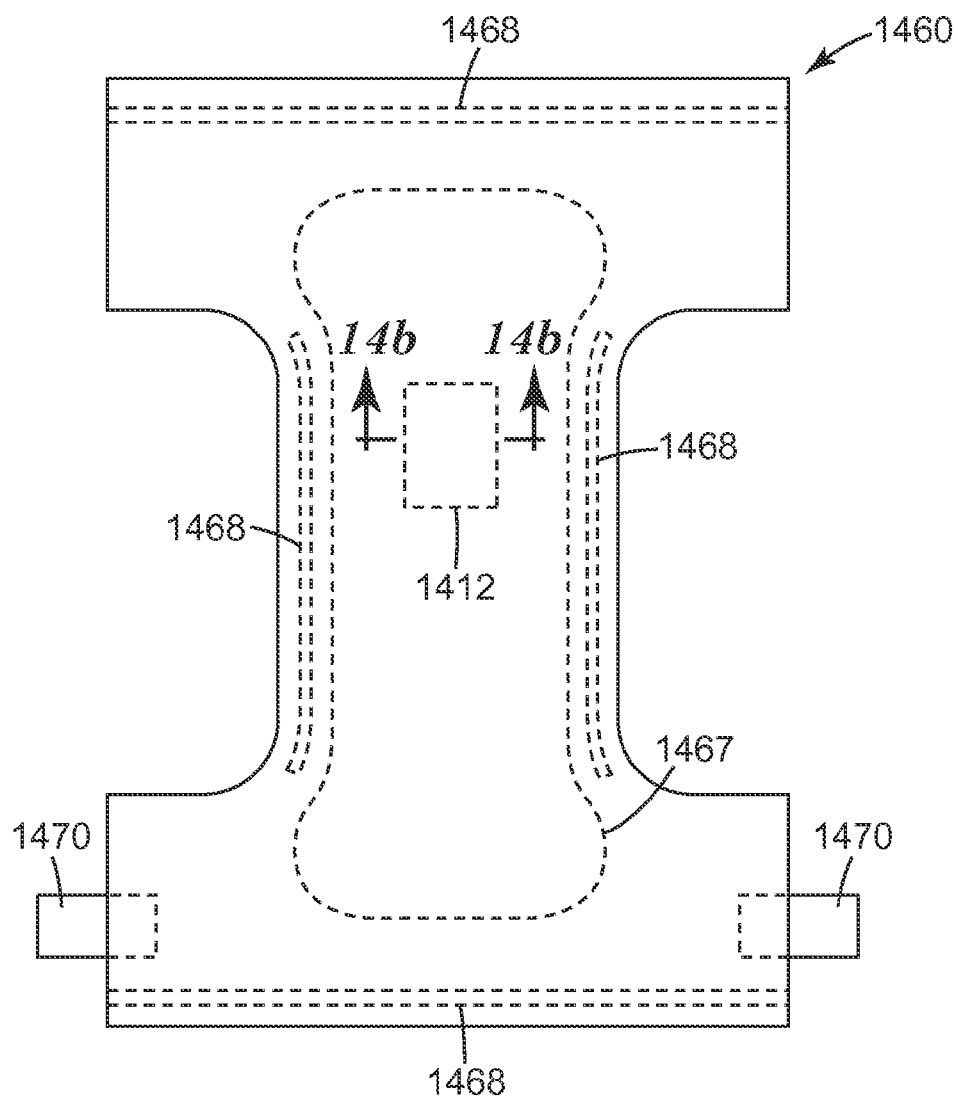
FIG. 14a is a schematic plan view of a diaper or similar incontinence garment.
Figure 14B:
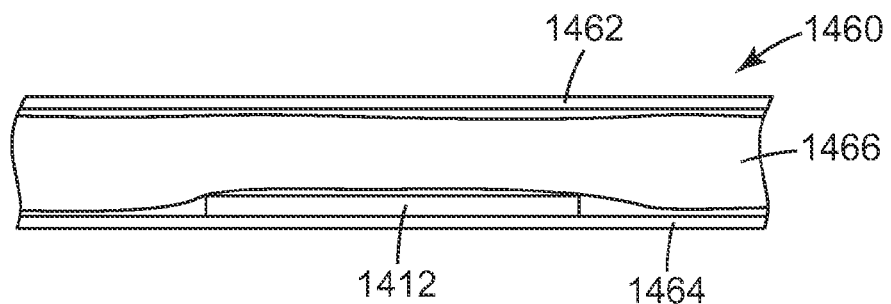

FIG. 14a is a schematic view of a diaper 1460 or similar incontinence or absorbent garment, and FIG. 14b is a schematic cross-sectional view taken along lines 14b-14b in FIG. 14a. The diaper includes a liquid-permeable inner sheet 1462, a liquid-impermeable outer sheet 1464, and an absorbent material 1466 trapped between the sheets 1462, 1464, and optionally limited to an absorbent region 1467. The diaper 1460 may also include elastic members 1468 and closure elements 1470 such as adhesive tape or hook-and-loop fasteners. The diaper has also been assembled in such a way as to include a wetness sensor 1412 at a position that is likely to become wet or soiled. The sensor 1412, which may be or comprise any of the wetness sensors disclosed herein, is disposed between the sheets 1462, 1464, and may be adhered to either such sheet using an adhesive, ultrasonic welding, or by other known attachment techniques. If the sensor 1412 is disposed between the liquid-impermeable sheet 1464 and the absorbent material 1466, it will degrade when the material 1466 is saturated and will not be triggered by the release of only a small amount of target fluid. The wetness of the diaper may be conveniently detected by remote monitoring of the sensor 1412 as discussed above.

In some cases it may be advantageous to design the sensor 1412 to have a large aspect ratio, e.g., even larger than those of FIGS. 4 and 6, by significantly lengthening the jumper (424, 624). With such an elongated sensor, the antenna or inductor (e.g., 418, 618) can be placed within the diaper at a position that is not likely to become wet or soiled, e.g., at a position closer to the waistband, while the remainder of the sensor (and in particular at least a portion of the jumper) may be placed at the position that is likely to become wet or soiled. Such placement of the antenna or inductor may also be used to improve communications (e.g., signal-to-noise ratio) with the reader device.

In alternative embodiments, any of the wetness sensors disclosed herein may additionally include a skin-compatible adhesive, such as a gentle silicone skin adhesive, on an outer surface of the sensor or on a portion of such outer surface. A sensor configured in this way may be applied directly to the skin of a subject rather than being manufactured into a diaper, brief, or other garment or article. Such an approach can potentially reduce overall cost and encourage implementation by working with existing garments and avoiding the need for specially manufactured garments or articles. The adhesive may also be formulated to be repositionable such that the attachment point of the sensor to the subject may be readily changed, and/or such that the sensor may be reused on a given subject between changings, for example. The adhesive may be applied selectively to a portion of the sensor at the antenna or inductor (e.g., 418, 618), and, particularly if the wetness sensor is elongated in shape, the remainder of the sensor may comprise no skin-compatible adhesive. In such an embodiment, the antenna or inductor portion of the sensor may be attached to the subject at or above the waist, for example, and the remainder of the sensor may be allowed to simply hang down into the diaper or brief as appropriate.

Any known skin-compatible adhesives may be used in such embodiments. In one embodiment, a skin-compatible adhesive may be prepared by blending 100 parts of polydimethylsiloxane (e.g., Xiameter brand OHX-4070) polymer with 30 parts MQ resin (e.g., type Belsil TMS 803, available from Wacker Chemie AG) to obtain a homogeneous mixture. The adhesive solution may be coated onto an outer surface of a wetness sensor (or a web containing numerous wetness sensors, see e.g. FIG. 1) using a simple knife coater or by other known means at a suitable thickness, e.g. 0.002 inches to 0.004 inches. Such an adhesive may be crosslinked by exposure to a suitable e-beam source, for example. Preferably, the skin-compatible adhesive is substantially electrically non-conductive such that it does not detrimentally affect the operation of the tuned RF circuit, even when applied directly to conductive traces of the sensor.

The sensors described herein may be especially useful when used in an infrastructure-based wetness monitoring system, e.g., a system that detects wetness in incontinent long-term care facility patients. In such a system, the state of the fluid sensor changes with the wetness condition of the personal hygiene article or other article to which it is attached, and the state of the sensor is communicated to a reader when interrogated. That information may then be communicated by the reader via a network connection to a central storage location. The database may store the information with a timestamp and/or other identification information. This information can then be post-processed using custom algorithms. Continence-related data from a multiplicity of sites can be collated, packaged, extracted, correlated, integrated, and analyzed for use by hospitals, care institutions, manufacturers of absorbent articles, governments, health insurers, and so forth. Exemplary wetness monitoring systems include but are not limited to the systems described in U.S. Pat. No. 7,250,547 (Hofmeister), U.S. Pat. No. 7,977,529 (Bergman), U.S. 2007/0270774 (Bergman) WO 2007/128038 (Bergman), WO 96/14813 (Bergman) and WO 2011/054045 (Bergman), all of which are incorporated herein by reference. The wetness monitoring systems are not limited to urine detection for incontinent patients, but also have applicability in the detection, monitoring, and management of conditions in which other fluids and exudates from the body (or from other sources) may be present, including wound management.

An exemplary system for monitoring incontinence in one or multiple subjects includes one or more fluid sensors installed into or on an item for which it is desired to monitor the presence of fluid, a reader that includes appropriate electronics and an antenna to couple the reader to the sensor(s), a network connection, and a database for storage and analysis of data. Another system comprises a display means; input means that may be operable by a user; one or more transmitters, each transmitter being associated with one or more subjects being monitored; the one or more transmitters being configured to transmit signals containing at least continence-related data for the multiple subjects, wherein the continence-related data has been obtained over time from one or more wetness sensor such as those disclosed herein that may be associated with an absorbent article worn by each respective subject; a receiver unit configured to receive signals from the one or more transmitters; and processing means in communication with at least the receiver unit, the processing means including a display processor configured to process the received signals and communicate display information to the display means for display of a visual representation of continence-related information derived from the wetness sensors attached to absorbent articles worn by the subjects being monitored.

Sensors may be of different types, e.g. where they have different functionality. In addition to wetness sensors, the sensors may include functionality for sensing one or more of temperature, pH, pressure, odor, bioanalytes, chemical or biological markers, and other indicators of the wellbeing of the subject. Potential sensors include sensors to detect for the presence of water, urine, blood, other liquid solvents, or elements therein. In addition, sensors for monitoring vital signs such ECG, blood glucose levels, blood pressure, pulse, etc. may be combined with the disclosed wetness sensors. An extensive list of clinically relevant medical conditions may be recognized by the detection of a number of metabolites, chemicals and ions, as well as other substances and cells of different types, in urine. Such materials as nitrites, amino acids, Beta-2 microglobulin, such measurements as pH, osmolality, white cell count, protein, specific gravity, and such conditions as multiple myeloma and haematuria, may be detected by testing urine from a patient using appropriate known sensors in combination with the disclosed sensors.

In one example system, the processing means may be configured to receive incontinence pad type information for an absorbent article worn by a subject and, based on the pad type indicator and the continence-related data, calculate a risk of wetness leakage from the absorbent article. A sensor status circuit may be combined with identifier circuitry, or it may be provided separately, to integrate information to identify the patient and/or the type of incontinence article being monitored. Information on the patient or type of absorbent article may be obtained through automated sensing or manual entry. The system may include separate input means to facilitate manual entry of non-wetness event data, including one or more actuators on the transmitter; optically, electronically, or otherwise scanning a code from a card or other reference guide, or manual entry of a code; wherein any of the foregoing are optionally performed using a hand held device. Additional means may be included to sense movement of the subject. The reader or transmitter may be combined with sensing means to determine changes in the position of the subject, including e.g. a position tracking device (such as GPS) and/or one or more motion detectors such as an accelerometer or pressure transducer providing an indication of movement of the subject. Such detectors may be configured to detect wandering or falls that are communicated to the processor in real time for notification to a caregiver.

Potential readers include both hand-held and fixed readers, including readers that are bed-mounted, chair-mounted (including e.g. wheel-chair mounted or rocking chair mounted), cart-mounted, wall-mounted, furniture mounted, or mounted on or in any other mobile or stationary support unit for a patient, where such readers may be battery-powered or powered by a wired connection to a wall socket, for example.

Processing means may be provided in a single processing device or may be provided by a number of discrete or connected processing units or processing elements in which each may perform different processing functions that contribute to the overall functionality of the system. As such, various functions of the processing means may be provided by various elements of the system including a processing element which may, in some embodiments, be associated with continence sensors per se, and/or a processing element contained within transmitters or receivers of the system, or a processing element provided as part of a "central monitor" in a particular site employing the system, or in communication with one of more of the foregoing by wired or wireless connection with other processing elements through wide area networks (WANs), local area networks (LANs), the Internet, and other networks as may be known in the art, including, for example, by proprietary RF link, wired Ethernet, wireless Ethernet, Zigbee, Bluetooth, etc. The database may be hosted locally at the customer site, remotely at a separate facility, or in the cloud. User interfaces are typically provided for report generation and statistical inquiries.

The processing means may be configured to cause an alert or otherwise provide feedback to the caregiver on the status of the sensor(s) so that the caregiver can attend to the subject being monitored. Alternately, or in addition, the processing means may be configured to automatically correlate patterns in continence-related data and non-wetness event data. The processing means may be configurable to receive inputs from multiple types of sensors. This may be achieved, for example, by collecting continence data from a sensor associated with an absorbent article worn by a subject; collecting non-wetness event data pertaining to the subject; and using the collected non-wetness event data and sensor data to optimize a mathematical model for monitoring incontinence in a subject, and using the optimized model to monitor incontinence in a subject wearing an absorbent article with a sensor of the current invention. In some embodiments, the processing means receive multi-site continence-related data obtained from a plurality of sites where the system is used to monitor subjects for incontinence. The processing means may include a data compiling processor receiving the multi-site continence-related data. The system may provide a data store for storing the multi-site data, and one or more network communication elements connecting the one or more sites with the data compiling processor. The processing means may utilize data obtained from the plurality of sites to perform analysis including: identifying trends in usage of absorbent articles; evaluating care assessments for subjects being monitored; identifying trends in caregiver behavior; identifying correlations between continence-related data, event data, and other conditions applicable to the group of patients; benchmarking performance of different incontinence products or different models of continence care, and so forth.

One example of a wetness detection system may include a wetness sensor installed into a brief, a bed-mounted reader including appropriate electronics and an antenna that is capable of coupling to the sensor, a wireless network connection, and a database for storage and analysis of data. The bed-based reader may include a resonance detection circuit and a tuned antenna installed in the bed, and may include a presence-sensing unit, such as a pressure sensor, to determine if the patient is in the bed. The wireless network connection can be a proprietary RF link, and the database may be stored on a machine that can be accessed by the care facility's network. Along with the database, the machine can run algorithms to conditionally monitor the data. One algorithm may report when patients become wet and automatically notify the health care staff. The system may collect information about each patient who is wearing a brief with the wetness sensor coupled to a bed-based reader, and may remotely log it in the database. With this type of continuous monitoring, compliance with existing standard F-TAG 315 is demonstrated since the minimum check-time of once every two hours is exceeded. The system may also automatically log when the brief is changed, as well as when the patient is in or out of bed. This information can be used to generate a typical routine for each patient. By utilizing this system and the automatic documentation and trend analysis, a more accurate predictive toileting schedule can be created. This may be more effective than attempting to train and schedule toilet activities around other activities such as eating or sleeping schedules.

There are several potential advantages and uses for such systems. The system may be used for training staff to perform duties, including: selecting a suitable absorbent article or pad type; using the system to monitor and/or assess incontinence sufferers; timely attendance to subjects with incontinence; evaluating a condition of a subject suffering incontinence; developing a continence care plan for a subject; and evaluating the effectiveness of a continence care plan. Day-to-day trends can be monitored, including required brief changes, average number of briefs used, time spent out of bed, average time wet before changed, and more, to develop predictive toileting schedules. Deviations from the trends can also be monitored. The processing means may be configured to correlate patterns in continence-related data and non-wetness data with one or more disease condition indicators and provide guidelines to investigate the presence of a disease state. Checking for anomalies could enable the prediction of health issues such as dehydration, UTIs, yeast infection, and so forth earlier than would be predicted without this system. This type of trend analysis can also help monitor the quality of care or help identify gaps in staffing. For instance, a high average time wet before change could indicate under-staffing at the health care facility. By monitoring the average number of briefs used, the average time wet before being changed, and the amount of insult in the brief, the system can predict which patients are at higher risk for developing skin/pressure ulcers.

The system can encourage additional checking and faster response times for these patients to minimize the escalation of their condition. The system can also automatically generate paperwork that is required should a skin/pressure ulcer form. This automatically-generated documentation may ensure that the patient's condition is properly reported so that further deterioration is minimized, and may bring visibility to the problem so that it does not go unnoticed during staff shift changes.

Unless otherwise indicated, all numbers expressing feature sizes, amounts, physical properties, and so forth used in the specification and claims are to be understood as being modified by the term "about". Accordingly, unless indicated to the contrary, the numerical parameters set forth in the specification and claims are approximations that can vary depending on the desired properties sought to be obtained by those skilled in the art utilizing the teachings of the present application.

Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if a cell depicted in a figure is turned over or flipped over, portions previously described as below or beneath other elements would then be above those other elements.

Various modifications and alterations of this invention will be apparent to those skilled in the art without departing from the scope and spirit of this invention, and it should be understood that this invention is not limited to the illustrative embodiments set forth herein.

The invention claimed is:

1. A sensor, comprising:
   a first substrate; and
   a tuned RF circuit carried by the first substrate, the RF circuit including a first conductive pattern, a first capacitor, and a jumper all disposed on a same side of the first substrate, the RF circuit being characterized by an impedance or resistance;
   wherein the first conductive pattern includes a coil, an inner terminus, and an outer terminus;
   wherein the jumper electrically couples the inner terminus to the outer terminus; and
   wherein the jumper includes a frangible link, and the impedance or resistance of the RF circuit changes by at least a factor of 5 when the frangible link is contacted by a target fluid.

2. The sensor of claim 1, wherein the first capacitor is part of the first conductive pattern.

3. The sensor of claim 2, wherein the first conductive pattern includes interdigitated conductive traces, and the interdigitated conductive traces form the first capacitor.

4. The sensor of claim 1, wherein the first capacitor comprises a discrete component electrically attached to the first conductive pattern.

5. The sensor of claim 1, wherein the jumper has a first and second terminus, and wherein the first capacitor comprises first and second capacitor plates, the first capacitor plate selected from one of the inner and outer terminuses of the first conductive pattern, and the second capacitor plate selected from one of the first and second terminuses of the jumper.

6. The sensor of claim 5, wherein the second terminus of the jumper has a direct electrical connection to the first conductive pattern.

7. The sensor of claim 5, wherein the first capacitor further includes a first dielectric material disposed between the first and second capacitor plates, and the first dielectric material is soluble in the target fluid to provide the frangible link.

8. The sensor of claim 1, the tuned RF circuit further including a second capacitor, wherein the jumper has a first and second terminus, and wherein the first capacitor has a first capacitor plate formed by the first terminus of the jumper and a second capacitor plate formed by the inner terminus of the first conductive pattern, and the second capacitor has a third capacitor plate formed by the second terminus of the jumper and a fourth capacitor plate formed by the outer terminus of the first conductive pattern.

9. The sensor of claim 8, wherein the first capacitor further includes a first dielectric material disposed between the first and second capacitor plates, and the second capacitor further includes a second dielectric material disposed between the third and fourth capacitor plates, and wherein both the first and second dielectric materials are soluble in the target fluid to provide the frangible link.

10. The sensor of claim 1, wherein at least a portion of the jumper is connected to the first conductive pattern of the first substrate by an adhesive material that is soluble in the target fluid to provide the frangible link.

11. The sensor of claim 10, wherein the adhesive material is electrically conductive.

12. The sensor of claim 10, wherein the adhesive material is electrically insulative.

13. The sensor of claim 1, wherein the jumper comprises a conductive member disposed on a jumper substrate.

14. The sensor of claim 13, wherein the jumper substrate is disposed between the conductive member and the first conductive pattern.

15. The sensor of claim 13, wherein the jumper substrate is adapted to dissolve, swell, or otherwise degrade in the target fluid to provide the frangible link.

16. The sensor of claim 13, wherein the jumper substrate is connected to the first substrate by an adhesive material that is soluble in the target fluid to provide the frangible link.

17. The sensor of claim 13, wherein the conductive member has a variable thickness.

18. The sensor of claim 13, wherein the jumper substrate has a structured surface, and wherein the conductive member is disposed on the structured surface.

19. The sensor of claim 1, wherein contact of the frangible link by the target fluid substantially renders the RF circuit inoperative.

20. The sensor of claim 1, further comprising a skin-compatible adhesive disposed on an outer surface of the sensor.

21. The sensor of claim 20, wherein the adhesive comprises silicone.

22. An absorbent garment comprising the sensor of claim 1.

23. The absorbent garment of claim 22, wherein the absorbent garment includes a liquid-permeable sheet, a liquid-impermeable sheet, and an absorbent material trapped between the liquid-permeable sheet and the liquid-impermeable sheet, and wherein the sensor is disposed between the liquid-permeable sheet and the liquid-impermeable sheet.

24. A construction article comprising the sensor of claim 1.

25. The article of claim 24, wherein the construction article is or includes wall board, insulation, flooring, roofing, and/or a fitting or support structure for a pipe.

26. A system, comprising:
   the sensor of claim 1; and
   a reader configured to remotely assess a condition of the tuned RF circuit.

27. The system of claim 26, wherein the reader is configured for mounting in or on a mobile or stationary support for a person.

\* \* \* \* \*